United States Patent [19]

Murtagh

[11] Patent Number: 5,688,669

[45] Date of Patent: Nov. 18, 1997

[54] METHODS FOR NUCLEIC ACID DETECTION, SEQUENCING, AND CLONING USING EXONUCLEASE

[76] Inventor: James J. Murtagh, 511 Calibre Woods Dr., Atlanta, Ga. 30329

[21] Appl. No.: 476,562

[22] Filed: Jun. 7, 1995

Related U.S. Application Data

[62] Division of Ser. No. 49,264, Apr. 19, 1993, Pat. No. 5,518,901.

[51] Int. Cl.$^6$ ............ C12P 19/34; C12N 15/10; C12N 15/66; C12Q 1/68

[52] U.S. Cl. ............ 435/91.2; 435/6; 435/172.3

[58] Field of Search ............ 435/91.2, 172.3, 435/6, 320.1

[56] References Cited

U.S. PATENT DOCUMENTS

| | | | |
|---|---|---|---|
| 4,683,195 | 7/1987 | Mullis et al. | 435/6 |
| 5,516,633 | 5/1996 | Fuller | 435/6 |
| 5,518,901 | 5/1996 | Murtagh | 435/91.2 |

OTHER PUBLICATIONS

Gyllensten et al. (1993). Methods in Enzymology 218:3–16.
Ward et al. (1989), Nucl. Acids Res. 17(20):8394.
White TJ, Madej, R, Persing DH. *Adv. Clin. Chem.* 1992;29–161–96.
Persing DH. *J. Clin. Microbiol.* 1991;29:1281–5.
Jung V, Pestka SB, Pestka S. *Nucleic Acid Res* 18:6156.
Zhang Y, Coyne MY, Will SG, Levenson CH, Kawasaki ES. *Nucleic Acids Res.* 1991;19:3929–33.
Helmuth R. Nonisotopic detection of PCR products. In: Innis MA, Gelfand DH, Sninsky JJ, White TJ (eds.), *PCR Protocols: A Guide to Methods and Applications.* San Diego, CA: Acedemic Press, 1990;119–28.
Gyllensten UB, Erlich HA. *Proc Natl Acad Sci USA* 1988;85:7652.
Stoker AW. *Nucleic Acids Res* 1990; 13:4290.
Aslanidis C, de Jong P. *Nucleic Acids Res* 1990;18:6069–74.
Kuijper *Gene* 1992;112:147–55.
Haun RS et al. *BioTechniques* 1992;13:515–8.
Haun R, Moss J. *Gene* 1992;112:37–43.
Pham T, Cheng QL. Clontechques 1993;8:5–9.
Lindahl T, Ljungquist S, Siegert W, Nyberg B, Sperens B. *J. Biol Chem* 1977;252:3286–94.
Rastchian A, Buchman GW, Schuster DM, Berninger MS. *Anal Biochem* 1992;206:91–7.
Rashtchian A, Thornton CG, Heidecker G. *PCR Methods Appl* 1992;2:124–30.
Nisson PE, Rashtchian A, Watkins PC. *PCR Methods Appl* 1991;1:120–3.
Wahlberg et al. *Proc Natl Acad Sci USA* 1990;87:6569–73.
Drake T, Hindler JA, Barton GW, Bruckner DA. *J Clin Microbiol* 1987;25:1442–5.
Yamane et al. *Nucleic Acids Symp. Ser.,* 1988; 19:93–95.

*Primary Examiner*—Nancy Degen
*Attorney, Agent, or Firm*—Needle & Rosenberg, PC

[57] ABSTRACT

The present invention provides a method of detecting the presence of a nucleotide sequence within a double-stranded DNA in a sample comprising: a. digesting the double-stranded DNA with an exonuclease which converts at least a portion of the double-stranded DNA to single-stranded DNA, b. binding the single-stranded DNA with a nucleic acid probe which selectively hybridizes with the single-stranded DNA, and c. detecting hybridization between the single-stranded DNA and the nucleic acid probe, the existence of hybridization indicating the presence of the nucleotide sequence within the double-stranded DNA in the sample. The present invention further provides a method of detecting the presence of a nucleotide sequence in a sample comprising DNA which is the product of a DNA amplification technique. The invention also provides methods of sequencing and cloning using exonuclease.

10 Claims, 13 Drawing Sheets

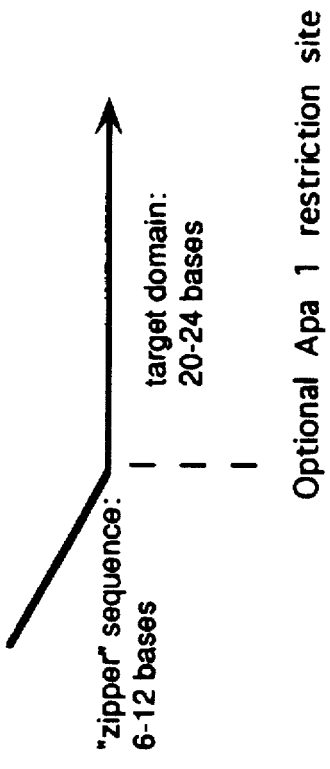
Figure 1A. Zippered Gene-Specific Primer (zgsp)
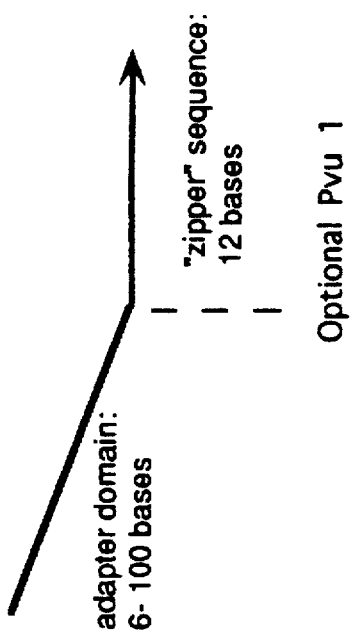
Figure 1B. Zipper Adapter Primer (zap)

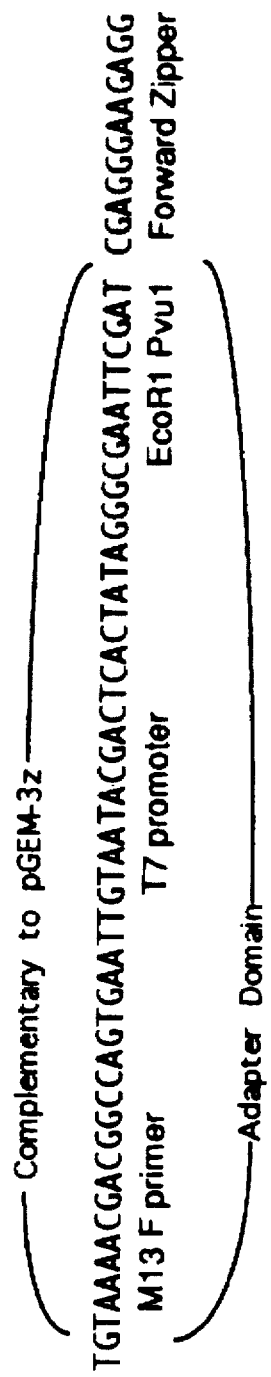
Fig. 5A) Zap-F
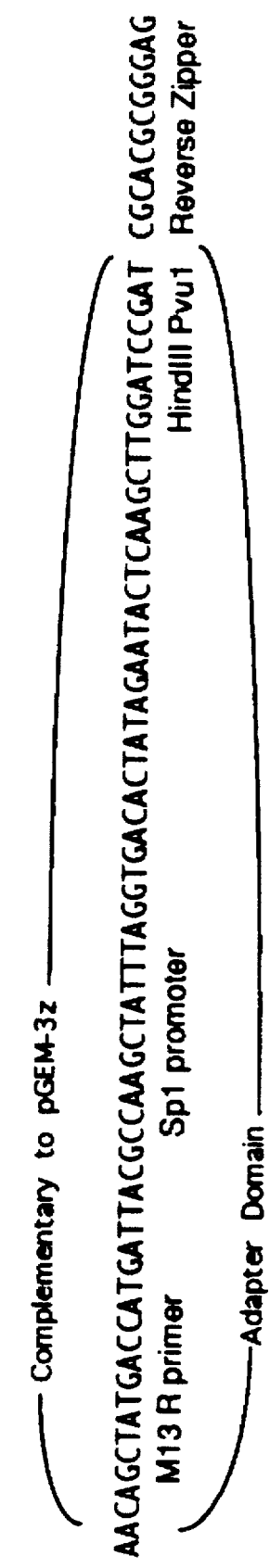
Fig. 5B) Zap-R

FIGURE 9.

```
Bam H1          Apa1              Hind III
GATCCATCGAGGGAAGAGAGGGCCCTCTCCCGCGTGCCA
    GTAGCTCCCTTCTCTCCCGGGAGAGGGCGCACGGTTCGA
```

FIGURE 13B.

```
CGAGGGAAGAGGTGCGGCCGC            AATTGCGGCCGC
           CGCCGGGCGTTAA            CGCCGGGCGTGGAGAAGGGGAGC

CGAGGGAAGAGGTGCGGCCGC            GATCGCGGCCGC
           CGCCGGGCGCTAG            CGCCGGGCGTGGAGAAGGGGAGC

CGAGGGAAGAGGTGCGGCCGC            AGCTGCGGCCGC
           CGCCGGGCGTCGA            CGCCGGGCGTGGAGAAGGGGAGC
```

*Note - same upper primer used in each case (blunt or sticky)
CGAGGGAAGAGAGGTGCGGCCGC Different lower primer used according to needs
GCGGCCGC         Blunt      zipper-adapter
AATTGCGGCCGC     EcoR I     zipper-adapter
GATCGCGGCCGC     BamH 1     zipper-adapter
AGCTGCGGCCGC     Hind III   zipper-adapter

METHODS FOR NUCLEIC ACID DETECTION, SEQUENCING, AND CLONING USING EXONUCLEASE

This application is a division of application Ser. No. 08/049,264, filed Apr. 19, 1993 now U.S. Pat. No. 5,518,901.

BACKGROUND OF THE INVENTION

DNA analytic and hybridization methods to specifically detect and identify small amounts of nucleic acids are now indispensable to molecular biology, the genetic engineering industry, and molecular medicine. Of these, procedures that amplify target nucleic acid sequences-such as the polymerase chain reaction (PCR)[1], ligase amplification, and transcription-based systems derived from PCR-have proven most effective[2].

Difficulties in critical analytic steps following DNA amplification, however, have prevented the technology from being more widely applied in clinical laboratories and the biotechnology industry. Analysis of DNA products following amplification usually takes one of three forms: (1) colorimetric hybridization analysis, (2) cloning, (3) direct sequencing[1-3]. Each of these procedures has proved more difficult than initially anticipated, in part because of special properties of amplified DNA that differ from nonamplified DNA. Numerous investigators have documented these well-known difficulties in analyzing amplified DNA, resulting from the following:

1. Complementary amplified DNA strands are usually uneven (or "ragged") because some strands are usually incompletely extended, and extraneous nucleotides are often added to 3' ends. "Ragged" DNA ends cannot be ligated to blunt end vectors, and is inefficiently bound by modifying enzymes[1-5].
2. Independently of the "raggedness" of DNA ends, base pairing at extreme DNA ends is believed to be unstable (an effect referred to as "breathing" of DNA ends). This effect appears to lead to increased susceptibility to exonuclease, and further difficulties in binding modifying enzymes, including restriction endonucleases. PCR-amplified DNA is widely found to cut inefficiently by many restriction endonuclease-including NotI, XbaI, XhoI, and SmaI-preventing analysis and cloning by many strategies[5].
3. Incompletely used substrates and reaction by products of amplification procedures can interfere with subsequent analysis. Interfering reactants include nucleotides and oligonucleotides; interfering byproducts include pyrophosphates.
4. Extraneous DNA, including "primer dimer," is often coamplified with target, confusing subsequent analysis and competing with target in cloning and sequencing steps. For this reason, amplified DNA must be extensively purified prior to these analytic procedures.
5. Amplified DNA strands tend to rapidly reanneal and exclude hybridized probes[1-3,6]. This effect has been noted to create special difficulties in the sequencing of double-stranded PCR products. Numerous strategies have been suggested for converting PCR fragments into single strands so that they can be more easily analyzed by hybridization, sequencing, and cloning, including asymmetric PCR and magnetic beads. However, none has proved entirely satisfactory.

Many strategies to circumvent difficulties in analyzing amplified DNA require oligonucleotide primers that have 5' modifications, such as chemical groups including biotin, digoxigenin and fluorescein that can aid in detection and/or purification of amplified DNA.

Other strategies require sequence additions, such as 40 nt GC clamps, RNA promoters, restriction endonucleases etc. Since the needs of individual experiments vary greatly, investigators often need several oligonucleotides of similar or identical 3' sequence targeted to particular genes under study, but have various different 5' modifications. The current invention aims in large part to simplify and unify many different protocols requiring different 5' additions to amplified DNA. Defined 6–12 base sequences are added to the 5' of each amplification primer. After resulting amplification, three defined 6–12 base sequences are used to attach universal zipper adapter primers, so that useful desired chemical groups and functional sequences can be easily added to amplified DNA. Thus, the invention is a unified, integrated system to create an "economy of primers," so that an individual amplification product can be used in many different capacities without resynthesizing amplification primers.

The invention also simplifies detection and characterization of amplified DNA. Previously, colorimetric PCR hybridization assays have been investigated as an alternative to gel electrophoresis and Southern blot analysis of PCR-amplified DNA. Such gels and Southern blots have proven too time-consuming and tedious for typical clinical laboratories[8]. Solid-phase colorimetric PCR assays capture denatured amplification products on probes bound to nylon membranes (as in "reverse dot blots"[6-7]) or to microtiter plates[2,3]. However, the sensitivity of these assays suffers due to the tendency of the denatured PCR product strands to reassociate and exclude oligonucleotide probes, and stearic interference between the bound oligonucleotides and the solid support, which impedes hybridization to nucleic acids in solution[5,6]. In some cases, colorimetric detection is improved by creating single-strand PCR products through asymmetric PCR that can associate with bound probes without interference[7,9]. Unfortunately, asymmetric PCR is notoriously difficult to reproduce, and does not lend itself to automation. Reamplification of the PCR product using internal or "nested" primers may improve assay sensitivity, but is costly, and compounds DNA contamination problems in clinical laboratories with concomitant false positive results.

Numerous different cloning procedures for analyzing amplified DNA can be found in the art, but all remain inefficient, expensive, and tedious. Restriction endonucleases do not cut PCR produced DNA well, and untreated PCR products cannot be cloned into blunt-end vectors unless the ragged ends of PCR are first repaired. Blunt end ligation is inefficient under any circumstances.[4]

"TA" cloning vectors exploit the 5' adenosine residues that are sometimes added to the 3' of PCR products to clone into a vector with thymidine residues (Invitrogen, San Diego, Calif.). Major problems with the use of these vectors includes instability of the terminal thymidine residue, inefficient transformation, and the limitation of using Taq polymerase to generate the terminal adenosine residues on the PCR product. Hybridization of single-base overhangs is inefficient, and these vectors do not work well in most laboratories.

Methods using T4 DNA polymerase to clone PCR products have recently been introduced into the art. These methods seek to introduce extended cohesive ends into PCR products complementary to mirror cohesive ends placed through recombinant methods into vectors. Stoker et al. performed PCR amplification with two primers which are homologous to the cohesive termini created by AccI and XmaI, respectively. The PCR products are treated with T4 DNA polymerase to remove 3' terminal sequences. After heat inactivation of the polymerase, the products are ligated to plasmid cut with AccI and XmaI[10]. Aslanidis et al. generated clonable PCR fragments with 5' ends containing an additional 12 nucleotide sequence which lacks dCMP[11]. After amplification, products were digested by T4 DNA polymerase in the presence of dGTP; the fragments thus have 5'-extending single-stranded tails of a defined sequence and length. In the same way, the plasmid vector was amplified with primers homologous to sequences in the multiple cloning site. The vector oligos have additional 12 nucleotide tails complementary to the tails used for fragment amplification, permitting the creation of single-stranded ends with T4 DNA polymerase in the presence of dCTP[11]. This was similar to the method of Kuijper et al. ("prime" cloning) who introduced sequences into plasmids and lambda phage deficient in the nucleotide dTTP[12]. After digestion with restriction endonucleases and T4 DNA polymerase in the presence of dTTP, these vectors accept PCR fragments with mirror cohesive ends. Other investigators have used this technique with variable success[13–15].

Each of the methods for cloning using T4 DNA polymerase suffers from severe difficulties. First, sequences to be made cohesive must be specially engineered into the vector either by PCR[11] or via gene construction[116]. These methods are therefore unsuitable for use with most commonly used vectors. Second, PCR products must be extensively purified prior to cloning. The 3' exonuclease of T4 DNA polymerase is active only in the absence of 3 of 4 nucleotide species. Third, T4 DNA polymerase is found to be quite labile, and most commercially available lots of this enzyme are found to be unsuitable for this purpose. Users of these methods have documented the need to test multiple enzyme lots prior to identifying suitable T4 enzymes.

Kaling et al. replaced T4 DNA polymerase with exonuclease III as an enzyme for creating cohesive ends in PCR cloning[5]. However, this procedure requires kinased primers, and generates very limited cohesive ends (4 bases) corresponding to 5' protruding restriction endonuclease sites in plasmid. This method is therefore restricted to plasmids with appropriate restriction endonuclease sites. In addition, exonuclease III is often found to contain single-strand nuclease activity that can digest away cohesive protruding single-strand ends and lower cloning efficiency.

Cloning procedure using uracil DNA glycosylase (UDG)[17] are found in the art[18–20]. However, these procedures apply only to specially constructed vectors containing uracil (dUTP). Specially constructed PCR primers made with uracil phosphoramidite are also required, material that is expensive and unavailable to many laboratories.

Analysis of amplified DNA sequence can also be accomplished by direct sequencing without cloning to vectors. However, most laboratories have found sequencing of double-stranded PCR product to be inefficient and unsuitable for routine use. Several methods for converting PCR fragments into single strands, including the asymmetric PCR protocol of Gyllensten and Erlich[9], the affinity strand separation method of Mitchell and Merrill[21], and the magnetic strand separation method of Uhlen and coworkers[22]. However, the efficiency of asymmetric PCR is notoriously variable from sample to sample, and the other methods require expensive materials including biotinylated primers and streptavidin-coated beads.

Consequently, there remain several needs in the art for DNA analytic procedures to specifically detect, identify, and manipulate amplified DNA. In DNA diagnostics, the greatest need is a rapid, economical, highly sensitive colorimetric DNA hybridization test to specifically detect amplification products without running electrophoresis gels or performing Southern blot experiments. Preferably, such a test could be performed in a format familiar to clinical laboratories, such as a microtiter plate, with greater sensitivity than current tests to detect denatured DNA. In many cloning experiments, a need exists for a convenient rapid procedure to flexibly recombine PCR-generated DNA into vector plasmids and bacteriophage with high efficiency, without the need to alter vector by addition of sequence, or alteration with restriction endonuclease. In other experiments, it is also important that vectors can be altered for rapid transfer of adapted DNA. The procedure needs to bypass the need for T4 DNA polymerase, an enzyme of variable efficiency and stability. PCR products should not require extensive purification. In sequencing, a need exists for a rapid method to convert amplified DNA partly or wholly into single strands without expensive or time-consuming protocols, and to extend the number of base sequences obtained per sequencing reaction. The present invention provides such methods as well as many related advantages.

SUMMARY OF THE INVENTION

The present invention provides a method of detecting the presence of a nucleotide sequence within a double-stranded DNA in a sample comprising: a. digesting the double-stranded DNA with an exonuclease which converts at least a portion of the double-stranded DNA to single-stranded DNA, b. binding the single-stranded DNA with a nucleic acid probe which selectively hybridizes with the single-stranded DNA, and c. detecting hybridization between the single-stranded DNA and the nucleic acid probe, the existence of hybridization indicating the presence of the nucleotide sequence within the double-stranded DNA in the sample. The present invention further provides a method of detecting the presence of a nucleotide sequence in a sample comprising DNA which is the product of a DNA amplification technique.

The invention also discloses a method of detecting the presence of a nucleotide sequence in a sample comprising: a. amplifying the nucleotide sequence using a first primer containing deoxyuridine monophosphate and a second primer not containing deoxyuridine monophosphate to yield a double-stranded DNA having a polyuridylated 5' end on one strand, b. partially disassociating the resultant double-stranded DNA with uracil DNA glycosylase to form a 3' overhang on the polyuridylated 5' end, c. digesting the double-stranded DNA with a 3' exonuclease which digests only a 3' strand from an end opposite the polyuridylated 5' end for a time sufficient to convert at least a portion of the double-stranded DNA to a single-stranded DNA, d. binding the single-stranded DNA with a nucleic acid probe which selectively hybridizes with the single-stranded DNA, and e. detecting hybridization between the single-stranded DNA and the nucleic acid probe, the existence of hybridization indicating the presence of the nucleotide sequence in the sample.

The present invention also provides a method of adapting a target DNA for subsequent manipulation comprising: a. annealing to the target DNA a first primer having a 3' terminal region homologous to a portion of the target DNA, and a 5' terminal region not homologous to the target DNA and of a length sufficient for future selective hybridization, b. amplifying the annealed target DNA and primer to yield double-stranded DNA, c. partially digesting the double-stranded DNA with a 5° exonuclease for a time sufficient to convert only a portion of the double-stranded DNA to single-stranded DNA having a 3' terminal sequence, d. selectively hybridizing a second primer with a portion of the 3' terminal sequence of the single-stranded DNA, wherein the second primer contains a functional group capable of subsequent manipulation, and e. contacting the partially digested primer-DNA hybrid with a DNA polymerase to form a contiguous double-stranded DNA containing the functional group, thereby adapting the double-stranded DNA for subsequent manipulation.

It is also a purpose of this invention to provide a method of adapting a nucleic acid for sequencing comprising: a. amplifying the nucleic acid using a first primer containing deoxyuridine monophosphate and a second primer not containing deoxyuridine monophosphate to yield a double-stranded DNA with a polyuridylated 5' end on one strand, b. partially disassociating the resultant double-stranded DNA with uracil DNA glycosylase to form a 3' overhang on the polyuridylated 5' end, c. digesting the double-stranded DNA with an 3' exonuclease which digests only the 3' strand from the end opposite the polyuridylated 5' end for a time sufficient to convert at least a portion of the double-stranded DNA to a single-stranded DNA, d. extending the partially digested 3' strand with a polymerase such that sequencing by a dideoxynucleotide process can be performed on the single-stranded DNA.

Furthermore, the invention provides a method of adapting a double-stranded DNA for insertion into a vector comprising digesting the double-stranded DNA in with a non-polymerasing DNA exonuclease for a time sufficient to create cohesive single-stranded DNA terminal regions which will hybridize with a vector having complementary cohesive single-stranded regions.

The present invention also provides a method of inserting a target DNA into a target vector for cloning comprising: a. annealing to the target DNA a first primer having a 3' terminal region homologous to a portion of the target DNA, and a 5' terminal region not homologous to the target DNA and of a length sufficient for future selective hybridization, b. amplifying the annealed target DNA and first prier to yield double-stranded DNA, c. denaturing the double-stranded DNA, d. hybridizing to the denatured DNA a second primer having a 3' terminal sequence homologous to the 5' terminal region of the amplified DNA, and having a 5' terminal sequence homologous to single-stranded regions of the target vector and not homologous to the target DNA or the 5' terminal region of the amplified DNA, e. amplifying the hybridized sequences to yield double-stranded insert DNA, f. digesting the double-stranded insert DNA with an exonuclease for a time sufficient to convert those sequences originating from the second primers to cohesive single-stranded insert DNA regions, g. hybridizing the cohesive single-stranded insert DNA regions with the target vector having homologous single-stranded regions to create a circular gapped vector-insert DNA hybrid, and h. transfecting the circular gapped vector-insert DNA hybrid into a host cell.

Furthermore, the invention provides a method of adapting a target vector for subsequent recombination comprising: a. annealing to a target DNA a first primer having (1) a 3' terminal region homologous to a portion of the target DNA (2) a 5' terminal region not homologous to the target DNA and of a length sufficient for future selective hybridization and (3) a sequence encoding a restriction endonuclease site located at the junction of the 3' terminal and the 5' terminal region of the primer, b. amplifying the annealed target DNA and first primer to yield double-stranded DNA, c. denaturing the double-stranded DNA, d. hybridizing to the denatured DNA a second primer having a 3' terminal sequence homologous to the 5' terminal region of the amplified DNA, and having a 5' terminal sequence homologous to single-stranded regions of the target vector and not homologous to the target DNA or the 5' terminal region of the amplified DNA, e. amplifying the hybridized sequences to yield double-stranded insert DNA, f. digesting the double-stranded insert DNA with an exonuclease for a time sufficient to convert those sequences originating from the second primers to cohesive single-stranded insert DNA regions, g. hybridizing the cohesive single-stranded insert DNA regions with the target vector having homologous single-stranded regions to yield a circular plasmid, h. transfecting the plasmid into a host cell, i. culturing the host cell containing the plasmid, j. purifying the plasmid from a lysate of host cell culture, k. contacting the plasmid with a restriction endonuclease which cleaves the site originating from the first primer such that the DNA originating from the first primer remains on the target vector, and l. exposing the target vector to an exonuclease for a time sufficient to create cohesive single-stranded DNA regions originating from the first primer on the vector, thereby adapting the vector for subsequent recombination.

Finally, the invention provides a method of adapting an insert DNA for subsequent recombination with a vector comprising: a. annealing to a target DNA a first primer having a 3' terminal region homologous to a portion of the target DNA, and a 5' terminal region not homologous to the target DNA and of a length sufficient for future selective hybridization, b. amplifying the annealed target DNA and first primer to yield double-stranded DNA, c. denaturing the double-stranded DNA, d. hybridizing to the denatured DNA a second primer having (1) a 3' terminal sequence homologous to the 5' terminal region of the amplified DNA, (2) a 5' terminal sequence homologous to single-stranded regions of the target vector and not homologous to the target DNA or the 5' terminal region of the amplified DNA, and (3) a sequence encoding a restriction endonuclease site located at the junction of the 3' terminal sequence and the 5' terminal sequence of the second primer, e. amplifying the hybridized sequences to yield double-stranded insert DNA, f. digesting the double-stranded insert DNA with an exonuclease for a time sufficient to convert those sequences originating from the second primers to cohesive single-stranded insert DNA regions, g. hybridizing the cohesive single-stranded insert DNA regions with the target vector having homologous single-stranded regions to yield a plasmid, h. transfecting the plasmid into a host cell, i. culturing the host cell containing the plasmid, j. purifying the plasmid from a lysate of host cell culture, k. contacting the plasmid with a restriction endonuclease which cleaves the site originating from the first primer such that the DNA originating from the first primer remains on the insert DNA, and l. exposing the target vector to an exonuclease for a time sufficient to create cohesive single-stranded DNA regions originating from the first primer on the vector, thereby adapting the insert DNA for subsequent recombination with a vector.

BRIEF DESCRIPTION OF THE DRAWINGS

FIG. 1 illustrates and defines the structures and terms used in many aspects of the invention. A Zipper-containing gene-specific primers (zgsp) are constructed with 20–24 bases complementary to target to be amplified. In some cases, the target-specific domain is followed by an Apa 1 restriction site, which may be used to strike target-specific sequence from additions. The 5' end of the primer consists of 6–12 bases defined as "zipper sequences" or "zippers." All "forward" or "upstream" gene-specific primers (defined as the PCR primer synthesized in the "sense" direction to the most 5' region of target DNA) are synthesized with 6–12 bases of the following sequence, defined as the "forward zipper": CGAGGGAAGAGG (SEQ ID NO:1). Each "reverse" or "downstream" gene-specific primer (defined as the PCR primer synthesized in the antisense orientation to target, and complementary to the 3' end of target) are synthesized with a different 6–12 bases of sequence, defined as the "reverse zipper": CGCACGCGGGAG (SEQ ID NO:2). Underlined sequence was found to be minimal nucleotide additions for the convertion. B. Zipper adapter primers (ZAPs) are constructed with 12-base zipper sequences at the 3'; thus, forward ZAPs have the sequence CGAGGGAAGAGG (SEQ ID NO:1) placed at the 3'; reverse ZAPs have the sequence CGCACGCGGGAG (SEQ ID NO:2) at the 3'. Following zipper sequences, most ZAPs are synthesized with a Pvu 1 restriction site, to permit cutting of insert from additions so that zipper sequence remains with insert. At the 5' of ZAPs are sequences including vector-specific sequences for cloning, T7 RNA promoters for transcription, sequence initiation sites, etc., on chemically modified nucleotides containing biotin, fluorescein, etc.

FIG. 5 illustrates a pair of zipper adapter primers (ZAPs) that have been proved particularly useful. A. ZAP-F is a 66-base oligonucleotide (SEQ ID NO:16) that can be attached to the forward (upstream) end of any zipper-containing DNA. Its sequence contains useful functional groups including an M13 forward universal sequencing primer (especially useful in dye-labeled DNA sequencing reactions in automated fluorescent sequencers), a T7 RNA promoter, EcoRI and Pvu 1 restriction sites. B. ZAP-R is an 81-base oligonucleotide (SEQ ID NO:17) containing an M13 reverse sequencing site, SP6 RNA promoter, HindIII and Pvu 1 restriction site. Sequences corresponding to zipper sequences, to which the adapters are targeted in GLUEE reactions or secondary PCR, are underlined. These adapters have been synthesized with and without biotin, so that either end can be easily attached to solid support. After these adapters have been attached to DNA, either strand can be transcribed into cRNA in either liquid or solid phase. DNA inserts can be sequenced by various mechanisms. The sequences of ZAP-F and ZAP-R can also be complementary to sequence at the insertion site of pGEM-3Z, so that sequences can be efficiently cloned using procedures shown in FIG. 8.

FIG. 9 illustrates construction of pZGEM (SEQ ID NO:63 and 64) by conventional cloning procedures.

DETAILED DESCRIPTION OF THE INVENTION

Figure 2:
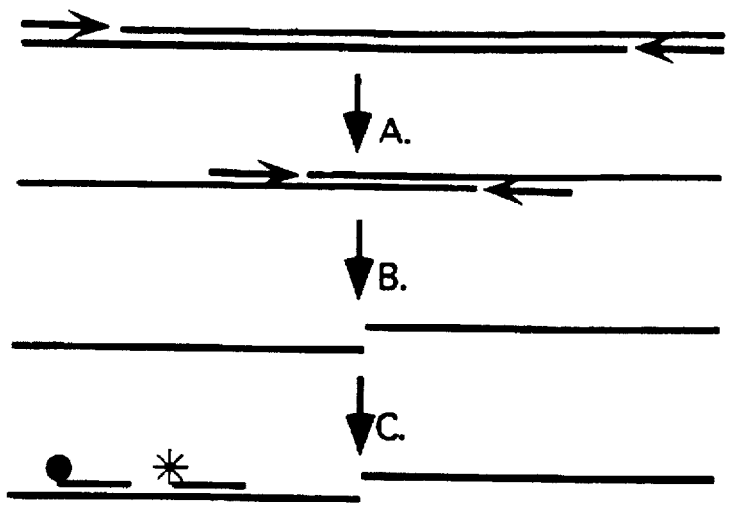
FIG. 2 illustrates an exonuclease-amplification coupled confirmation technique (EXACCT), in format A. A. DNA is digested partially or to completion using exonuclease. Direction proceeds from the end of both strands of double-stranded DNA in standard buffers used for amplification. B. Digestion is complete when exonuclease digestion meets near the middle of the PCR product; the exonuclease is unable to alter single-stranded nucleic acids, so digestion is terminated. C. Two separate oligonucleotides complementary to sequence in the first third of the PCR product are solution-hybridized to digested PCR product. One oligonucleotide is biotin-labeled (●) and serves to bind the complex to a solid support. The other nucleotide bears a detector group (*) such as digoxigenin, fluorescein, or $^{32}P$ moiety, etc. The method can be used in detecting amplified DNA, segments of restricted repetitive DNA, as from mitochondria, and in capturing and detecting highly repetitive ribosomal rRNA as in a detection scheme for mycobacteria.

The present invention provides a method of detecting the presence of a nucleotide sequence within a double-stranded DNA in a sample comprising: a. digesting the double-stranded DNA with an exonuclease which converts at least a portion of the double-stranded DNA to single-stranded DNA, b. binding the single-stranded DNA with a nucleic acid probe which selectively hybridizes with the single-stranded DNA, and c. detecting hybridization between the single-stranded DNA and the nucleic acid probe, the existence of hybridization indicating the presence of the nucleotide sequence within the double-stranded DNA in the sample. An example of this method is shown in FIG. 2.

By "selective hybridization" it is meant that hybridization only substantially occurs with the targeted nucleic acid. Thus, through "selective hybridization" one can detect the presence of a target nucleic acid in an unpure sample. The preferred length of the nucleic acid probes is about 20 bases with an optimum functional range from about 12 to 100 bases. Various exonucleases may be selected for use in this method including T7 gene 6, exonuclease III, T4 DNA polymerase, non-recombinant T7 DNA polymerase, and lambda exonuclease.

The nucleic acid probes utilized in these methods may be labeled with a detectable moiety, and hybridization determined by detecting the presence of the detectable moiety. The single-stranded DNA may also be bound with at least two selectively hybridizing nucleic acid probes which bind unique regions on the single-stranded DNA. Additionally, a first nucleic acid probe can be labeled with biotin and a second nucleic acid probe can be labeled with a detectable moiety, and hybridization determined by binding the biotin on a streptavidin-coated solid support, removing unbound DNA and second probe, and detecting the presence of the moiety of the second probe which is bound to the DNA. The nucleic acid probes may be bound to solid support, such as biotin, either before or after hybridization through either covalent or non-covalent attachment of probe to solid support. The detectable moiety can be selected from a wide range of detectable substances including digoxigenin, fluorescein, acridineester, radioactive isotopes, or enzymes.

Depending on the location of desired probe hybridization the double-stranded DNA can be contacted with an exonuclease for a time sufficient to convert the entire double-stranded DNA to single-stranded DNA. The amount of time required will therefore vary from about 30 seconds to over 10 minutes or more, depending on the length of double-stranded DNA necessary to convert to single strands.

The present invention described above can likewise be applied to a method of detecting the presence of a nucleotide sequence which is the product of a DNA amplification technique. Various amplification techniques which are contemplated include, for example, polymerase chain reaction, ligase chain reaction, transcription amplification system, isothermal chain reaction based on RNA transcription.

Figure 3:
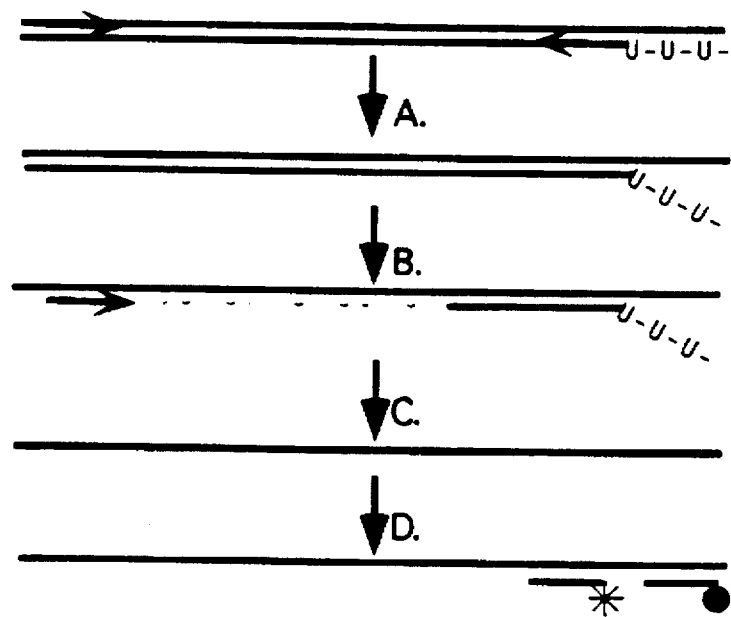
FIG. 3 illustrates a second exonuclease-amplification coupled DNA diagnostic scheme in format B. In this invention, one primer used to amplify DNA bears a polyuridine (U) tail. A. Treatment of DNA with UDG creates a 3' overhang, protecting that DNA end from digestion with exonuclease III. B. Exonuclease III digestion proceeds from nonprotected end. C. Complete digestion of the uridine-containing strand leaves a complementary full-length single-strand DNA D. Two separate oligonucleotides are hybridized to the protected single-strand DNA, similar to FIG. 1. Other strategies to selectively protect one end of the DNA molecule from exonuclease digestion can also be used, such as introduction of phosphothioate linkages into 5' or 3' ends of oligonucleotides.

The invention also discloses a method of detecting the presence of a nucleotide sequence in a sample comprising: a. amplifying the nucleotide sequence using a first primer containing deoxyuridine monophosphate and a second primer not containing deoxyuridine monophosphate to yield a double-stranded DNA having a polyuridylated 5' end on one strand, b. partially disassociating the resultant double-stranded DNA with uracil DNA glycosylase to form a 3' overhang on the polyuridylated 5' end, c. digesting the double-stranded DNA with a 3' exonuclease which digests only a 3' strand from an end opposite the polyuridylated 5' end for a time sufficient to convert at least a portion of the double-stranded DNA to a single-stranded DNA, d. binding the single-stranded DNA with a nucleic acid probe which selectively hybridizes with the single-stranded DNA, and e.

detecting hybridization between the single-stranded DNA and the nucleic acid probe, the existence of hybridization indicating the presence of the nucleotide sequence in the sample. FIG. 3 provides an example of this method.

The preferred number of uracils to be attached to the polyuridylated 5' end is between 4 and 6 but should be at least 3. A particularly useful exonuclease is exonuclease III. The time recommended for digestion is between 1 and 10 minutes, but may be between 30 seconds and 30 minutes. The double-stranded DNA may be contacted with exonuclease for a time sufficient to convert the entire double-stranded DNA to single-stranded DNA. Depending upon the length of the DNA and the location of the primer hybridization region, this time may be greater than 10 minutes.

The present invention also provides a method of adapting a target DNA for subsequent manipulation comprising: a. annealing to the target DNA a first primer having a 3' terminal region homologous to a portion of the target DNA, and a 5' terminal region not homologous to the target DNA and of a length sufficient for future selective hybridization, b. amplifying the annealed target DNA and primer to yield double-stranded DNA, c. partially digesting the double-stranded DNA with a 5' exonuclease for a time sufficient to convert only a portion of the double-stranded DNA to single-stranded DNA having a 3° terminal sequence, d. selectively hybridizing a second primer with a portion of the 3' terminal sequence of the single-stranded DNA, wherein the second primer contains a functional group capable of subsequent manipulation, and e. contacting the partially digested primer-DNA hybrid with a DNA polymerase to form a contiguous double-stranded DNA containing the functional group, thereby adapting the double-stranded DNA for subsequent manipulation. An example of this method is provided in FIG. 4.

An example of the first primer, or zipper gene specific primer (zgsp) is given in FIG. 1.A. The zgsp's 5' terminal region is preferably between 6–20 bases especially between 6–12 bases. The 3' region is preferably 20–24 bases but may be 14 to 60 bases. Partial digestion with the 5' exonuclease generally can take between 5 seconds and 1½ minutes, but preferably is allowed to proceed for between 30 seconds and 1 minute. An example of the second primer, or zipper adapter primer (zap) is shown in FIG. 1.B. Preferably, the 5' sequence of the zap is between 6 and 100 bases, more preferably 10 to 40 bases. The 3' sequence may generally be between 6 to 12 bases, with 12 bases preferred. Partial digestion with the exonuclease generally occurs with the range of 5 seconds to 1½ minutes, especially within the range of 30 seconds to 1 minute. The 5' exonuclease is T7 gene 6 in a preferred method. The functional group may be a detectable moiety selected from the group consisting of fluorescein, digoxigenin, biotin, radioactive isotopes, acridineesters, and enzymes. Alternatively, the functional group can be selected from the group consisting of GC clamps, RNA transcription promoters, M13 sequencing primer sites, the Kozak consensus sequence for protein expression, biotin, uridines, and DNA binding protein recognition sites. Also, the functional group may be DNA encoding a restriction endonuclease recognition site.

Figure 14:
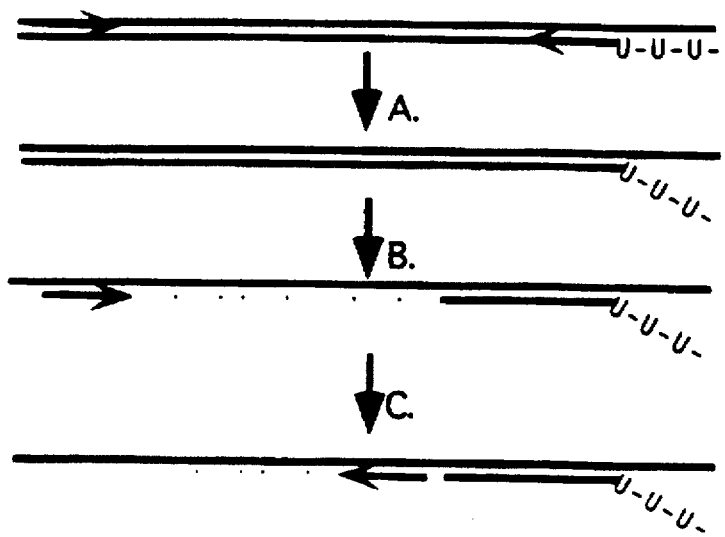
FIG. 14 illustrates sequencing using the present invention with a combination of UNG and ExoIII enzymes. A. 3' overhangs are produced in DNA that contains uridines at one end only (as in FIG. 3). B. Exonuclease III digestion for different time points creates variable-length 5' overhangs. C. After exonuclease III digestion is terminated by heating, sequencing can commence from the variable-length strand.

It is also a purpose of this invention to provide a method of adapting a nucleic acid for sequencing comprising: a. amplifying the nucleic acid using a first primer containing deoxyuridine monophosphate and a second primer not containing deoxyuridine monophosphate to yield a double-stranded DNA with a polyuridylated 5' end on one strand, b. partially disassociating the resultant double-stranded DNA with uracil DNA glycosylase to form a 3' overhang on the polyuridylated 5' end, c. digesting the double-stranded DNA with an 3' exonuclease which digests only the 3' strand from the end opposite the polyuridylated 5' end for a time sufficient to convert at least a portion of the double-stranded DNA to a single-stranded DNA, d. extending the partially digested 3' strand with a polymerase such that sequencing by a dideoxynucleotide process can be performed on the single-stranded DNA. An example of this method is shown in FIG. 14.

Figure 15:
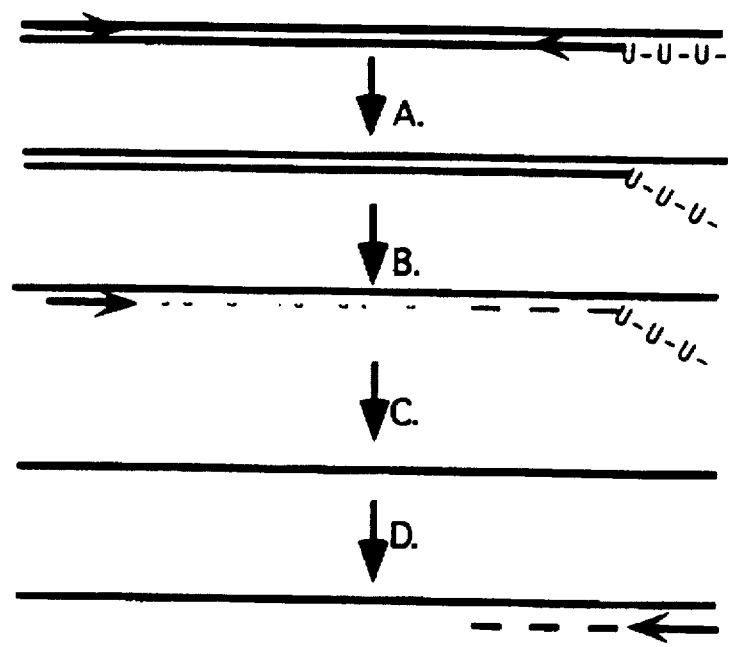
FIG. 15 illustrates sequencing by the method illustrated in FIG. 14 when one strand has been completely digested. A. 3' overhangs are produced in DNA that contains uridines at one end only (as in FIG. 3). B. Exonuclease III digestion for different time points creates variable-length 5' overhangs. C. After complete digestion of the susceptible DNA strand, the protected DNA strand consists of a full-length single strand. D. Sequencing primer is annealed to the remaining strand so that dideoxy sequencing may commence.

The preferred 3' exonuclease is exonuclease III. The preferred number of uracils to be attached to the polyuridylated 5' end is between 4 and 6 but should be at least 3. A particularly useful exonuclease is exonuclease III. The time recommended for digestion is between 1 and 10 minutes, but may be between 30 seconds and 30 minutes. The invention also provides that digestion may continue for a time sufficient to convert the entire double-stranded DNA to single-stranded DNA, followed by binding the single-stranded DNA with a nucleic acid primer which selectively hybridizes with the single-stranded DNA, such that sequencing by a dideoxynucleotide process can be performed on the single-stranded DNA. Depending upon the length of the DNA and the location of the primer hybridization region, this time will usually be greater than 10 minutes. This alternative method is shown in FIG. 15.

Furthermore, the invention provides a method of adapting a double-stranded DNA for insertion into a vector comprising digesting the double-stranded DNA with a non-polymerasing DNA exonuclease for a time sufficient to create cohesive single-stranded DNA terminal regions which will hybridize with a vector having complementary cohesive single-stranded regions. The amount of time required is between about 5 seconds and 90 seconds. In this method, the non-polymerasing DNA exonuclease is preferably T7 gene 6. This method allows for digesting the double stranded DNA in a solution that has not been purified by the removal of free deoxynucleotides, since the exonuclease is non-polymerasing.

The present invention also provides a method of inserting a target DNA into a target vector for cloning comprising: a. annealing to the target DNA a first primer having a 3' terminal region homologous to a portion of the target DNA, and a 5' terminal region not homologous to the target DNA and of a length sufficient for future selective hybridization, b. amplifying the annealed target DNA and first primer to yield double-stranded DNA, c. denaturing the double-stranded DNA, d. hybridizing to the denatured DNA a second primer having a 3' terminal sequence homologous to the 5' terminal region of the amplified DNA, and having a 5' terminal sequence homologous to single-stranded regions of the target vector and not homologous to the target DNA or the 5' terminal region of the amplified DNA, e. amplifying the hybridized sequences to yield double-stranded insert DNA, f. digesting the double-stranded insert DNA with an exonuclease for a time sufficient to convert those sequences originating from the second primers to cohesive single-stranded insert DNA regions, g. hybridizing the cohesive single-stranded insert DNA regions with the target vector having homologous single-stranded regions to create a circular gapped vector-insert DNA hybrid, and h. transfecting the circular gapped vector-insert DNA hybrid into a host cell. This overall method is diagrammed in FIGS. 7 and 8.

An example of the first primer, or zipper gene specific primer (zgsp), is given in FIG. 1.A. The zgsp's 5' terminal region is preferably 6–12 bases. The 3' region is preferably 20–24 bases but generally may be 14 to 60 bases. Partial digestion with the 5' exonuclease generally may take between 5 seconds and 1½ minutes, but preferably is allowed to proceed for between 30 seconds and 1 minute. An example of the second primer, or zipper adapter primer (zap) is shown in FIG. 1B. Preferably, the 5' sequence of the zap is between 6 and 100 bases, more preferably 10 to 40 bases, and the 3' sequence generally may be between 6 to 12 bases, with 12 bases preferred. Partial digestion with the exonuclease generally occurs with the range of 5 seconds to 1½ minutes, especially within the range of 30 seconds to 1 minute. The method can be practiced by transfecting the DNA hybrid to a host cell for repairing nucleotide gaps by naturally occurring enzymes.

Figure 10:
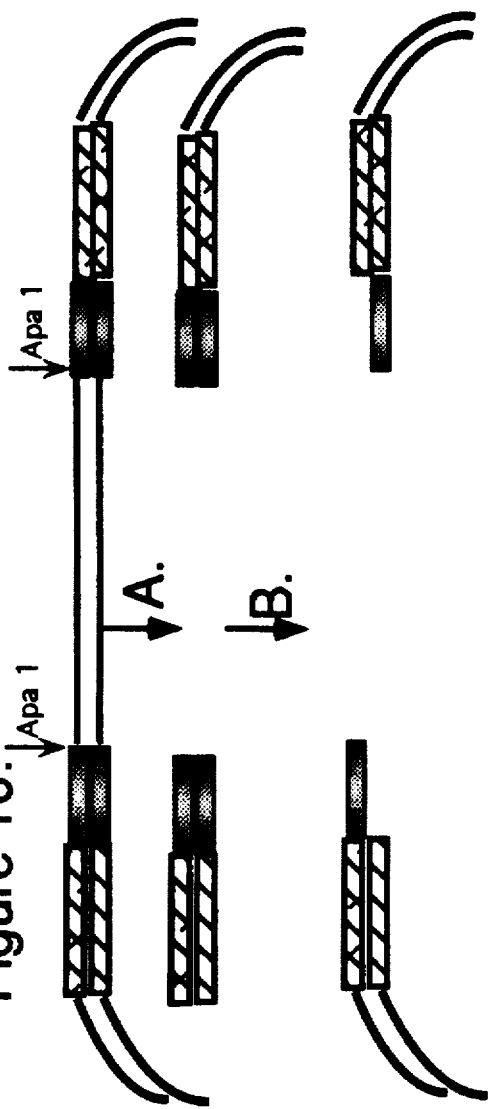
FIG. 10 illustrates creation of a vector with zipper-cohesive ends. Recombinant plasmids with zipper-bearing inserts (such as from FIG. 5) are engineered to contain restriction sites (in the example, the restriction site Apa 1 has been used) at the target with boundary (arrow). A. Digestion of plasmid with Apa 1 followed by B. exonuclease treatment generates a vector with zipper-sequence that can anneal to any complementary cohesive zipper-containing DNA containing ends. B. Exonuclease treatment yields cohesive ends.

Furthermore, the invention provides a method of adapting a target vector for subsequent recombination comprising: a. annealing to a target DNA a first primer having (1) a 3' terminal region homologous to a portion of the target DNA (2) a 5' terminal region not homologous to the target DNA and of a length sufficient for future selective hybridization and (3) a sequence encoding a restriction endonuclease site located at the junction of the 3' terminal and the 5' terminal region of the primer, b. amplifying the annealed target DNA and first primer to yield double-stranded DNA, c. denaturing the double-stranded DNA, d. hybridizing to the denatured DNA a second primer having a 3' terminal sequence homologous to the 5' terminal region of the amplified DNA, and having a 5' terminal sequence homologous to single-stranded regions of the target vector and not homologous to the target DNA or the 5' terminal region of the amplified DNA, e. amplifying the hybridized sequences to yield double-stranded insert DNA, f. digesting the double-stranded insert DNA with an exonuclease for a time sufficient to convert those sequences originating from the second primers to cohesive single-stranded insert DNA regions, g. hybridizing the cohesive single-stranded insert DNA regions with the target vector having homologous single-stranded regions to yield a circular plasmid, h. transfecting the plasmid into a host cell, i. culturing the host cell containing the plasmid, j. purifying the plasmid from a lysate of host cell culture, k. contacting the plasmid with a restriction endonuclease which cleaves the site originating from the first primer such that the DNA originating from the first primer remains on the target vector, and l. exposing the target vector to an exonuclease for a time sufficient to create cohesive single-stranded DNA regions originating from the first primer on the vector, thereby adapting the vector for subsequent recombination. This method is generally shown in FIG. 10.

An example of the first primer, or zipper gene specific primer (zgsp), is given in FIG. 1.A. The zgsp's 5' terminal region is preferably 6–12 bases and the 3' region is preferably 20–24 bases but may be 14 to 60 bases. Partial digestion with the 5' exonuclease may generally take between 5 seconds and 1½ minutes, but preferably is allowed to proceed for between 30 seconds and 1 minute. An example of the second primer, or zipper adapter primer (zap) is shown in FIG. 1.B. Preferably, the 5' sequence of the zap is between 6 and 100 bases, more preferably 10 to 40 bases, and the 3' sequence may be between 6 to 12 bases, with 12 bases preferred. Partial digestion with the exonuclease generally occurs with the range of 5 seconds to 1½ minutes, especially within the range of 30 seconds to 1 minute. In one embodiment of this method the restriction endonuclease is Apa 1. The invention contemplates that DNA repair generally occurs through native repair mechanisms.

Figure 11:
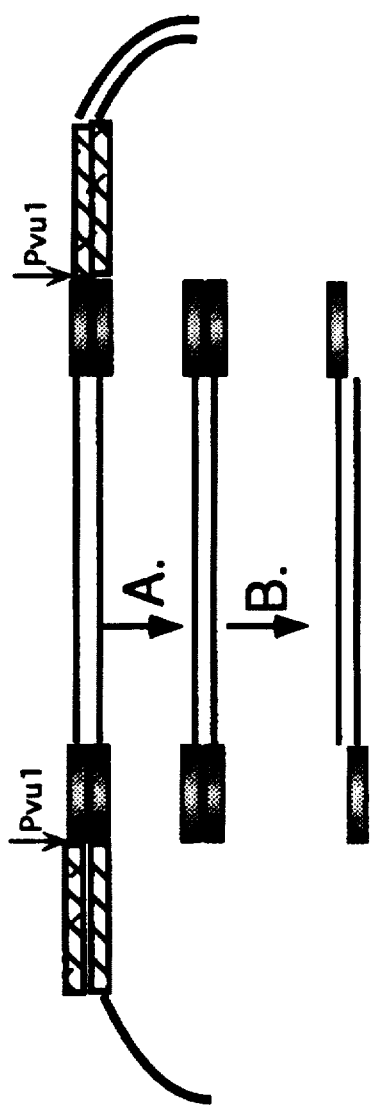
FIG. 11 illustrates regeneration of inserts containing zipper-cohesive ends from plasmids without further PCR. In our example, PCR primers and adapters were engineered to create Pvu 1 sites at the zipper-vector boundary. After digestion with A. Pvu 1 and B. exonuclease, cohesive zippers are again created, so that insert can be shuttled to any zipper-containing vector (as created in FIG. 10). Cohesive inserts may also be Joined to additional adapters(by GLUEE (FIG. 4) or by secondary PCR (FIG. 7), then cloned into vectors that have not been previously altered with zipper sequence.
Figure 12:
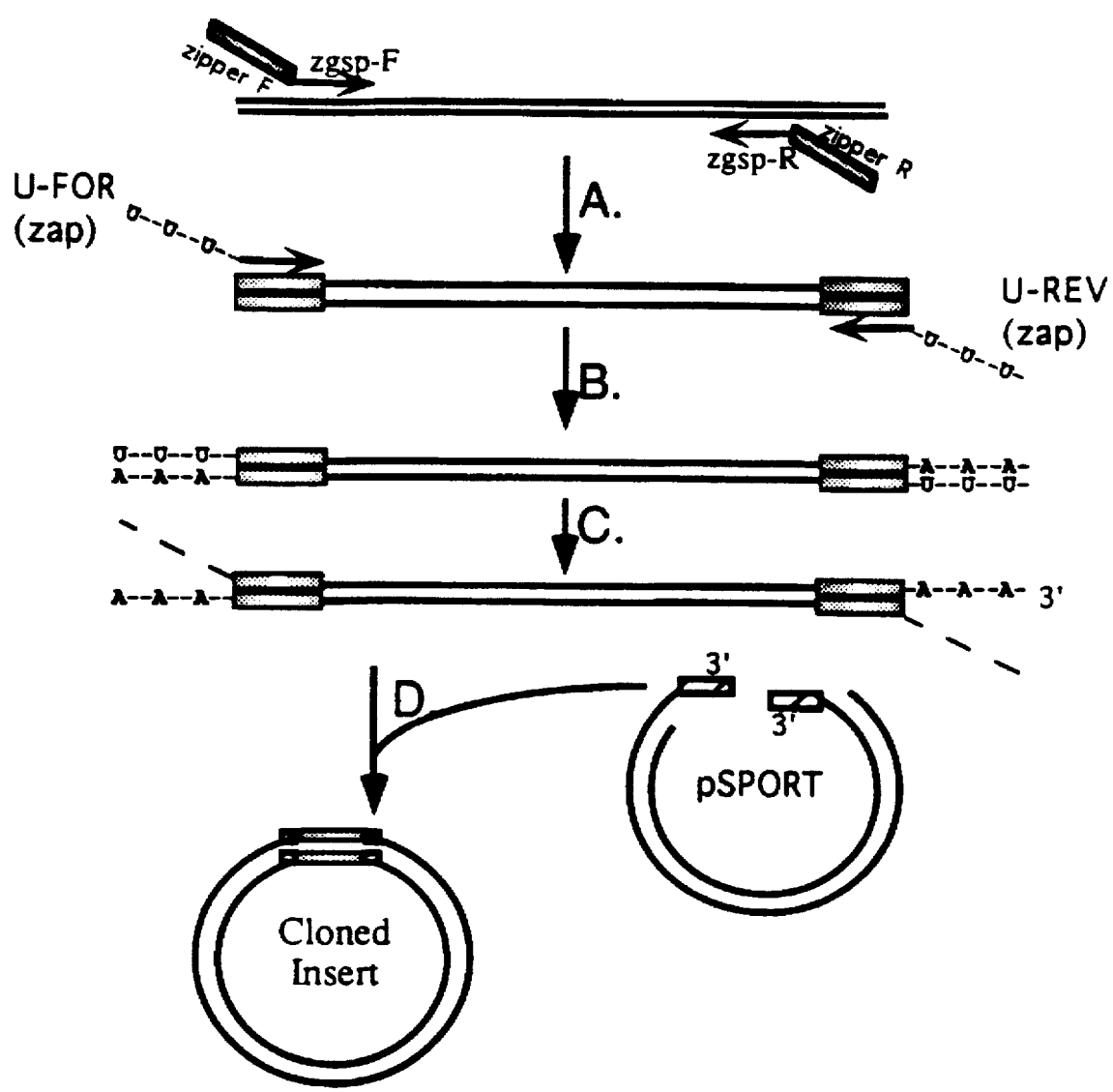
FIG. 12 illustrates utility of zipper adapters as an adjunct in cloning into vectors containing uridine. Procedures in the art exist to clone via digestion of uridines by uridine DNA glycosylase (UDG). However, such procedures require many PCR primers to be made with uridine, an expensive proposition that is not feasible for many laboratories. Using the invention, universal adapters containing uridines are attached to zipper-containing DNA (using methods of FIG. 3). Resulting DNA can be treated by UDG and cloned. A. Primary amplification of target using zipper containing gene-specific primers (zgsp). B. Secondary amplification using zipper adapter primers (ZAPS) containing uridines (U-FOR and U-REV). C. Digestion of double-strand PCR product with UDG to create cohesive ends. D. Cloning of PCR product into complementary cohesive ends of pSPORT vector (BRL, Bethesda, Md.).

Finally, the invention provides a method of adapting an insert DNA for subsequent recombination with a vector comprising: a. annealing to a target DNA a first primer having a 3' terminal region homologous to a portion of the target DNA, and a 5° terminal region not homologous to the target DNA and of a length sufficient for future selective hybridization, b. amplifying the annealed target DNA and first primer to yield double-stranded DNA, c. denaturing the double-stranded DNA, d. hybridizing to the denatured DNA a second primer having (1) a 3' terminal sequence homologous to the 5' terminal region of the amplified DNA, (2) a 5' terminal sequence homologous to single-stranded regions of the target vector and not homologous to the target DNA or the 5' terminal region of the amplified DNA, and (3) a sequence encoding a restriction endonuclease site located at the junction of the 3' terminal sequence and the 5' terminal sequence of the second primer, e. amplifying the hybridized sequences to yield double-stranded insert DNA, f. digesting the double-stranded insert DNA with an exonuclease for a time sufficient to convert those sequences originating from the second primers to cohesive single-stranded insert DNA regions, g. hybridizing the cohesive single-stranded insert DNA regions with the target vector having homologous single-stranded regions to yield a plasmid, h. transfecting the plasmid into a host cell, i. culturing the host cell containing the plasmid, j. purifying the plasmid from a lysate of host cell culture, k. contacting the plasmid with a restriction endonuclease which cleaves the site originating from the first primer such that the DNA originating from the first primer remains on the insert DNA, and l. exposing the target vector to an exonuclease for a time sufficient to create cohesive single-stranded DNA regions originating from the first primer on the vector, thereby adapting the insert DNA for subsequent recombination with a vector. This method is depicted in FIG. 11.

In one embodiment of this method the restriction endonuclease is Pvu 1. An example of the first primer, or zipper gene specific primer (zgsp), is given in FIG. 1.A. The zgsp's 5' terminal region is preferably 6–12 bases and the 3' region is preferably 20–24 bases but may generally be 14 to 60 bases. Partial digestion with the 5' exonuclease may generally take between 5 seconds and 1½ minutes, but preferably is allowed to proceed for between 30 seconds and 1 minute. An example of the second primer, or zipper adapter primer (zap) is shown in FIG. 1.B. Preferably, the 5' sequence of the zap is between 6 and 100 bases, preferably 10 to 40 bases, and the 3' sequence may generally be between 6 to 12 bases, with 12 bases preferred. Partial digestion with the exonuclease generally occurs with the range of 5 seconds to 1½ minutes, especially within the range of 30 seconds to 1 minute.

Briefly stated, the present invention provides methods to improve analysis of amplified nucleic acids. Three types of critical DNA analytic procedures are improved:

1. Specific detection of DNA sequences by colorimetric hybridization
2. Cloning of amplified DNA into vectors without the use of restriction enzymes or DNA ligase enzyme
3. Sequencing of amplified DNA In each case, partial or full digestion of double-strand PCR product with specific exonuclease under specific conditions is found to enhance analytic procedures. It is found that adapters can be usefully combined with exonuclease-treated DNA to improve capture of DNA molecules to solid support, and to enhance recombination of nucleic acids. Such exonuclease and adapter-mediated recombination of molecules can be used to incorporate diverse functional groups into DNA, including but not limited to useful nucleotide sequences (40-base GC clamps, 17-base RNA promoters, restriction endonuclease recognition sites, M13 sequencing primer sites, the Kozak consensus sequence for protein expression, etc.), chemically modified nucleotides (containing biotin, fluorescein, digoxigenin, uradines, etc.), and DNA binding protein recognition sites (such as that for GCN4).

In DNA diagnostics applications, this invention converts double-stranded DNA to single strands by incubation with exonuclease. T7 gene 6 (an example of a 5' exonuclease) is a preferred enzyme for this application, but exonucleases with either 5' or 3' activity that selectively bind to double-strand DNA, and digest the DNA to single strands without digesting the resulting single-strand DNA, can be used. The resulting single-strand DNA is then highly reactive with oligonucleotide probes, which can then be used to capture DNA to solid support (microtiter plates, coated magnetic or agarose particles, treated nylon or glass, etc.). Each step proceeds efficiently and rapidly in standard buffers used for PCR. Following conversion to single strands and specific capture, a second oligonucleotide can be used to detect the complex. In principle, the hybridization assay is similar to other colorimetric hybridizations previously used to detect denatured double-strand DNA. However, simple conversion to single strands by exonuclease is found to enhance colorimetric hybridization signal by 100-fold (Example 1), resulting in greater specificity, and is more convenient and automatable than procedures commonly used to denature PCR products.

For DNA cloning, the current invention provides a convenient method to introduce DNA into plasmid and bacteriophage vectors without using ligase, is independent of T4 DNA polymerase, does not require construction of special vectors, and does not require extensive purification of PCR product. The method also provides a means of joining DNA to adapter oligonucleotides bearing functional groups such as biotin, fluorescein, GC clamps, RNA promoters, etc. In this method, PCR primers are synthesized to which two different defined sequences (named "zippers," 6–12 bases in length) (FIG. 1.A.) can be synthesized at the 5' of gene-specific primer pairs (one defined zipper sequence at the 5' of all upstream gene-specific primers, the second at the 5' of all downstream gene-specific primers). After amplification, the product is treated briefly with 5' exonuclease (such as T7 gene 6) to create cohesive 3' overhangs. Adapter oligonucleotides of variable length, ranging from 6 to 100 nucleotides, can be annealed to the defined zipper sequence, and then extended by polymerase (e.g., Klenow fragment, T7 DNA polymerase, Taq polymerase, etc.). In this way, common sequences can be catalogued and then conveniently affixed to PCR products according to individual needs of particular experiments. Sets of adapters can be constructed containing sequence matching vector insertion sites; after affixing vector sequences to PCR fragment via exonuclease-extension, PCR fragment is easily cloned to the desired vector by (1) homologous recombination or (2) further treatment with exonuclease. Step 2 can be accomplished by 5' or 3' exonuclease in presence or absence of dNTPs. Individual PCR fragments can be shuttled into heterogeneous vectors by affixing different sets of adapters. Once cloned, inserts can be released from vector, affixed to a new set of adapter, and recloned into a different vector without reamplification. Alternatively, the same reaction may be used to affix adapters to vector in preparation to accept zipper-containing PCR products. The same reaction used to recombine insert with vector can join several different DNA inserts together, or affix sequences and modified nucleotide groups to inserts in vitro.

The present invention also provides improved methods for sequencing DNA. In one embodiment, a highly reliable 3' overhang is produced at one end of a DNA molecule by attachment of an oligonucleotide containing uridines, then treating with uridine DNA glycosylase (UDG). Immediately following, the DNA molecule is digested from the opposite 3' end with exonuclease III for variable lengths of time. After stopping the reaction and removing of exonuclease, dideoxy sequencing can commence from the variably digested end. This application of the invention results in greatly extended ability to sequence DNA ends, permitting >800 bases of sequence to be obtained per reacted DNA.

Thus, the invention offers combinations of exonuclease enzymes, zipper-defined sequences on PCR primers, and adapter oligonucleotides to produce a highly flexible, unified approach for cloning, sequencing, expressing, and detecting DNA. The catalog of primers created for this integrated system can be used with extreme economy. These and other aspects of the present invention will become evident upon reference to the following detailed description and attached drawings.

The following examples are offered by way of illustration, not by way of limitation.

EXAMPLE 1

Detection of parvovirus B19 by the Exonuclease Amplification Confirmation Capture Technique (EXACCT)

The strategy shown (FIG. 2) was used to detect parvovirus B10, the etiologic agent of *Erythema infectiosum*[25-26] from a bank of tissue or serum specimens using primers and amplification procedure previously described[27,28], yielding a 284 bp product. Following PCR amplification, three identical reaction aliquots (320 ml or ~400 mg DNA) were digested with exonuclease for 15 min at room temperature, electrophoresed, and transferred to nylon under nondenaturing conditions. To test the efficiency of exonuclease digestion-dilution, undigested PCR product was compared to product digested with 4 U/ml exonuclease, 0.4 U/ml, and 0.04 U/ml, and to single-strand PCR product produced using reduced P1 and excess P6 in asymmetric PCR. After gel electrophoresis, these DNA products were assessed by ethidium staining and by nondenaturing Southern blot analysis. The agarose gel used to size separate DNA was not exposed to alkali prior to transfer, Southern blot capillary, so that only single-strand DNA would be efficiently detected by the digoxigenin-labeled oligonucleotide probe. Double-strand DNA not exonuclease-treated was poorly detected compared to product treated by exonuclease or amplified by asymmetric PCR.

These same DNAs were detected (FIG. 6) in streptavidin-coated plates. Twenty ml of PCR product was added to 200 ml of hybridization buffer (4xSSC, 20 mM Hepes, 2 mM EDTA, 0.15% Tween20) containing both biotinylated (100 ng/ml) and digoxigenin-labeled (200 ng/ml) probes. Hybridization reactions were performed at 45° C. for 1 h. As in other colorimetric detection protocols previously in the art, double-stranded PCR products were heat-denatured at 95° C. for 5 min prior to hybridization. Single-stranded PCR products produced by asymmetric PCR or by exonuclease digestion were not heat-denatured. Equal amounts of control DNA amplified from an unrelated region of the B19 gene were treated with exonuclease in parallel. Following hybridization, 100 ml of each mixture was added to duplicate from an unrelated gene that was exonuclease-treated in parallel with experimental samples. Following hybridization, 100 ml of each mixture was added to duplicate wells of a streptavidin-coated microtiter plate prepared by coating with 200 mg of biotinylated BSA in 100 ml PBS/well overnight at 4° C., washed with PBS containing 0.15% Tween20, then saturated with 1000 mg of streptavidin in 100 ml PBS with 0.5% gelatin/well for 1 h at room temperature with shaking. The plate was then washed and 100 ml/well of 3,3',5,5'-tetramethyl-benzidine chromogen solution was added and incubated at room temperature. The color development was stopped after 15 min with 100 ml/well 2M phosphoric acid, and the plates read at 450 nm in a MR5000 Microplate reader (Dynatek, Chantilly, Va.).

Results of this experiment showed that single-strand PCR product produced by exonuclease treatment was detected in this format with 100× sensitivity of the denatured double-strand PCR product. Signal (in OD units) for DNA treated with exonuclease (T7 gene 6, 0.04 U/ml–4 U/ml) varied from 1.3 to >2.0 OD units. Signal for denatured double-strand DNA was ~0.15 OD units. Control DNA did not give appreciable signal, whether heat- or exonuclease-treated.

After establishing that the procedure enhances PCR signal using a wide range of exonuclease activities, we tested the invention on a panel of geographically dispersed serum samples collected from seronegative and seropositive individuals suspected of being infected by parvovirus B10 on clinical grounds. This pool was also studied by single-round PCR (35 cycles total) followed by Southern blot analysis, and by extended PCR with nested primers (60 cycles total). B19 copy number in the infected sera (20 cycles total) was estimated by comparison to parallel amplification of known amounts of B19 DNA diluted in serum. Samples positive by single-round PCR were found to contain 350–3,500 B19 genomes, while those negative by single PCR but positive by nested PCR contained as few as 3–30 copies of B10. In side-by-side comparison, we have found that the invention detected 3–30 copies of B10 after a single PCR from these clinical specimens, and from known amounts of B19 DNA diluted in serum. Single round PCR followed by the invention was at least 100-fold more sensitive than single-round PCR alone, 10–50 times as sensitive as Southern analysis of single-round PCR products, and equivalent in sensitivity to nested PCR. The invention required considerably less time, effort, and technical skill than Southern blot analysis of PCR products (<3 h for the invention versus >2 days for Southern analysis) and was more specific, since two separate probes are required to hybridize to target DNA in EXACCT detection. Compared to nested PCR, the risk of contamination was dramatically lessened, since PCR tubes are not opened between PCR rounds. The risk of false-positive carryovers due to carryover of PCR-amplified DNA can be further reduced by UNG treatment, whereas UNG cannot be used in both rounds of a nested PCR. Signal detection also appeared to correlate more quantitatively with the number of B19 genomes initially present in samples compared to nested PCR, which gave the same maximal signal regardless of the amount of B19 present.

The results demonstrate greatly enhanced ability to make sensitive, specific, and convenient diagnosis of human parvovirus B19 infection in seronegative immunocompromised individuals. DNA detection is done simply without gel electrophoresis on blot analysis in microtiter plates, a familiar, convenient format for clinical laboratories that can be easily automated. This procedure can easily detect a large number of other viruses and microorganisms by PCR, differentiate PCR-amplified polymorphic human DNA, and detect mutations in genetic disease.

Modifications of this strategy (FIG. 3) have been useful in protecting selected DNA strands, such that one strand is digested completely and the other is left intact. A tail of 5' uridines was synthesized at the 5' of the downstream parvovirus B19 amplifying primer. After PCR, the resulting DNA (300 mg) was treated in the same reaction vial used for amplification (without changing buffer) with *E. coli* UDG (10 U/reaction) (Bethesda Research Laboratories, Bethesda, Md.), to create a 3' overhang. The uracil containing end of the DNA was thus protected against 3' exonuclease attack during digestion with ExoIII (10 U/reaction, 37° C. for 10 min) (New England Biolabs, Wilmington, Del.). The resulting single-strand DNA was then hybridized under the same conditions described for format A above (FIG. 2), and signal detected in the microtiter plate. Results were identical to detection with T7 gene 6, demonstrating that both 3' and 5' exonucleases can successfully enhance DNA detection by hybridization. In Example 1, digestion of both strands by a single enzyme in format A produced the desired effect. For detection of shorter DNAs, it is evident that format B might be advantageous to protect the full length of one strand, such that sufficient length of DNA is presented to hybridizing capture and detection probes.

EXAMPLE 2

Detection and Specification of Mycobacteria Based on Exonuclease-Coupled Amplification The method of Example 1 was applied to detect mycobacteria genes amplified from clinical specimens. Two different mycobacterial genes were targeted, including *Mycobacteria tuberculosis* (MTB) IS6110 transposon and the gene for the mycobacterial 16S ribosomal (r)RNA subunit. Sample preparation, amplification procedures, and PCR primers were as previously described for the MTB IS61109 by Eisenach et al.[30]. The 16S ribosomal amplifications were as previously described[31] based on sequence catalogued[32,33]. After amplification, PCR products (20 ml, containing ~50 mg DNA) were treated with T7 gene 6 exonuclease (0.4 U/sample) then hybridized to capture and detect oligonucleotides using conditions described in Example 1. Sequence of capture probe for the IS6110 was digoxigenin-labeled probe 5'-Dig-AGTAATTCCGGACAACGCTC (SEQ ID NO:3) and biotin-labeled 5'-Bio-TTTCACGAACAACGCGACAA (SEQ ID NO:4). Sequence of capture probe for 16S rRNA PCR products was digoxigenin-labeled 5'-Dig-ACGGTGCCCGCAAAGTGTGG (SEQ ID NO:5) and biotinylated 5'-Bio-ACCGTGAGGGCATCGAGGTG (SEQ ID NO:6). Results demonstrated the extreme sensitivity of this procedure in specifically identifying PCR-amplified DNA. Control DNA amplified from unrelated genes were not detected by this procedure.

The flexibility of the system has been tested using different materials as solid support matrix. The exonuclease-treated DNA oligonucleotide hybrids have been captured to streptavidin-coated magnetic microspheres (Dynal M-280 particles, Oslo, Norway) and to streptavidin-coated microspheres packed in columns and pipette tips (U.S. Biochemical, Cleveland, Ohio). In each case, signal detection is markedly enhanced by the step of converting the DNA into single strands via exonuclease treatment. Other streptavidin-coated support matrices are currently under investigation, including streptavidin-coated glass, streptavidin-coated microtiter prongs, and streptavidin-coated nylon. It is thought that the mechanism by which the capture oligonucleotide is bound to solid support is not important, and that oligonucleotides covalently linked to support matrices without streptavidin should be equally effective. We have also demonstrated that oligonucleotides can be bound to matrix prior to hybridization of digested DNA.

EXAMPLE 3

Detection of Mycobacterial rRNA without PCR

Nucleic acids expressed at high copy numbers can be detected in cells without in vitro amplification. In this example, mycobacteria culture grown on agar slant or in BACTEC[34] broth were lysed by sonication using the procedure of Drake and others[35,36]. Immediately following the capture and detection probes described in Example 2 for 16S rRNA were hybridized to the released mycobacterial 16S rRNA. Since it is known that such rRNA is present at 15,000 copies per bacterium, it was felt that amplification would not be necessary to detect this nucleic acid[32]. For this example, the detection oligonucleotide was $^{32}$P-labeled by terminal deoxytransferase using standard procedures. 16S rRNA oligonucleotide hybrids were captured to streptavidin-coated microspheres. Results showed that the capture-detection technique clearly distinguished mycobacteria from other bacteria such as pseudomonas (a frequent contaminant of mycobacterial cultures) from both broth and culture. Other techniques, such as Gen-Probes (Gen-Probe, San Diego, Calif.) also can detect mycobacteria grown on agar slants via hybridization to species-specific acridine probes. However, substances from broth and in clinical specimens are found to interfere with detection by Gen-Probes; thus, the Gen-Probes system has not proved useful in early mycobacterial detection[35]. The current invention overcame this limitation by capturing the single strand 16S rRNA to solid support, so that inhibitors are washed away prior to detection. The capture of nucleic acids to solid support by the present invention can enhance detection by numerous different kinds of probes, including acridine-labeled probes.

The potential of detecting other high copy number nucleic acids by the invention without amplification can be performed. Mitochondrial DNA can be linearized by restriction endonuclease digestion or by sonication. Then, linearized double-strand DNA can be converted to single strands via exonuclease, captured to solid support, and detected with second labeled oligonucleotide. Some species of mRNA or genomic DNA could also be detected by this invention without amplification.

EXAMPLE 4

Figure 4:
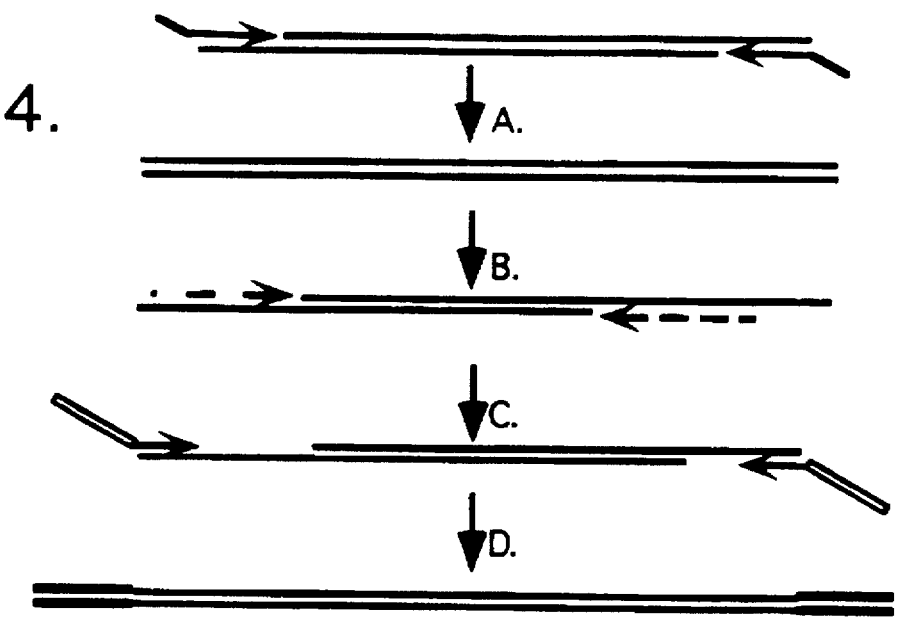
FIG. 4 illustrates a general ligation using exonuclease extension (GLUEE). A. DNA is amplified by zipper-containing gene specific primers (zgsp) PCR primers containing zippers (6–12 base defined sequences) at the 5'. E. PCR product is treated briefly with a 5' exonuclease, such as T7 gene 6 to create cohesive ends that span the zipper sequence. C. Adapter primers targeted to zipper sequence are annealed at room temperature. D. Extension of adapter primers on zipper-cohesive ends produce double-strand DNA containing functional groups introduced through adapters. A small amount of adapters can be used to introduce desired sequences into innumerable different amplification products.

Recombination of Human G Protein to Several Different Adapters Bearing Functional Groups and Vector-Complementary Sequence FIG. 4 depicts a General Ligation Using Exonuclease-Extension (GLUEE). This procedure has been used to join more than 15 different cDNAs coding for segments of human guanine nucleotide binding ("G") proteins and G protein coupled receptors to several different adapter oligonucleotides bearing functional sequences and modified chemical groups. In each case, the cDNA to be recombined was amplified using primers consisting of 20 bases specific to target (zipper-containing gene-specific sequence, or zgsp), FIG. 1.A., and continuing at the 5', an additional 6–12 bases referred to as "zippers." Each upstream gsp PCR primer was synthesized with a portion of "zipper forward" at the 5' (CGAGGGAAGAGG) (SEQ ID NO:1)=the underlined portion representing the minimal sequence to be attached). Each downstream PCR primer was synthesized with a portion of "zipper reverse" (CGCACGCGGGAG) (SEQ ID NO:2). After amplification, each PCR fragment had incorporated these zipper sequences at the 5' that could be used as targets for further amplification or to create cohesive ends. "Zipper adapters" (ZAPs, FIG. 1.B.) refer to variable-length oligonucleotides containing the zipper sequences at the 3' and commonly used sequences and chemical groups following. Thus, the 3' of the ZAPs overlap matching zipper sequences present at the 5' of the gene-specific PCR primers. The zipper containing amplified DNA is treated briefly with a 5' exonuclease (such as T7 gene 6). After generating cohesive ends of variable length, ZAPs can be hybridized. At room temperature, we have found that 6-base-complementarity between cohesive-end DNA and ZAP primers are sufficient to assure good hybridization. After hybridization, the adapter primer can initiate fill-in DNA synthesis via fresh DNA polymerase. DNA is extended in both directions, leading to double-strand DNA including the sequences and chemically modified nucleotides uncompounded into the ZAP.

The aspect of the invention described in this example has been used on numerous DNAs under varying conditions. PCR primers can be removed prior to exonuclease extension via microcon concentration or via ethanol precipitation. Initially, this step was designed so that remaining zgsp primers do not compete with ZAPs in exonuclease extension. However, in most cases we have found removal of PCR primer unnecessary. Untreated amplification product can be digested with T7 gene 6 exonuclease (0.4 U/reaction) in standard PCR buffers for 1 min at room temperature[23,24]. After this digestion, the exonuclease is heat-inactivated at 70° C. for 5 min. ZAP primers are then added (0.5–5 pmole) and annealed to DNA for 10 min at room temperature. Fresh DNA polymerase (Klenow fragment, Taq polymerase, etc.) is added, again without changing buffers.

This invention was used to join adapters to 400, 700, and 1,100 bp segments of human $G_q$ and $G_{11}$ protein cDNA amplified from cell lines derived from small cell lung tumors and from human umbilical cord endothelial (HUVEC) cells. Several different adapters were used (Table 1). One set of adapters (FAQ and RAQ) were used to introduce sequence complementary to the multicloning insertion site of protein expression vector QE9. Another set of adapters (FAB and RAB) introduce sequence complementary to the multicloning site of pET protein expression vectors. These adapters proved useful in several different ligase-free cloning strategies, ultimately permitting expression of amplified cDNA with 6-histidine amino terminal tags that can be used in protein affinity purification strategies.

One set of adapters (FAQ and RAQ) were used to introduce sequence complementary to the multicloning insertion site of protein expression vector QE9. Another set of adapters (FAB and RAB) introduce sequence complementary to the multicloning site of pET protein expression vectors. These adapters proved useful in several different ligase-free cloning strategies, ultimately permitting expression of amplified cDNA with 6-histidine amino terminal tags that can be used in protein affinity purification strategies.

TABLE 1

Sequences of oligonucleotides

Zipper sequences

| | | |
|---|---|---|
| zipper Forward | CGAGGGAAGAGG | (SEQ ID NO:1) |
| zipper Reverse | CGCACGCGGGAG | (SEQ ID NO:2) |

Zipper adapters

| | | |
|---|---|---|
| GC-For | CGCCCGCCGCGCCCCGCGCCCGGCCCGCCGCCCCGCCGGGCCC GAGGGAAGAGG | (SEQ ID NO:7) |
| RF-f | AGGGAGACCGGAATTCGGATCCCATATGGCGGCCGCGATCGAGG GAAGAGG | (SEQ ID NO:8) |
| RE-R | GACAGAGCACA GAATTCGGATCCAAGCTTCGATCGCACGCGGGAG | (SEQ ID NO:9) |
| U-FOR | CAUCAUCAUCAUCAUGCGATCGAGGGAAGAGG | (SEC ID NO:10) |
| U-REV | CUACUACUACUACGAT CGCACGCGGGAG | (SEQ ID NO:11) |
| FAB | CATCATCACAGCAGCGGCCTGGTGCCGCGCGGCGGCGCGATCGAG GGAAGAGG | (SEQ ID NO:12) |
| RAB | TCAGCTTCCT TTCGGGCTTTGTTAGCAGCCGGATCCGATCGCAC GCGGGAG | (SEQ ID NO:13) |
| FAQ-9 | AACTATGAGAGGATCGCATCACCATCACCATCACGGATCCTCGATC GAGGGAAGAGG | (SEQ ID NO:14) |
| RAQ-9 | GGATCTATCAACAGGAGTCCAAGCTCAGCTAATTAAGCTTCG ATCGCACGCGGGAG | (SEQ ID NO:15) |
| Zap-F | TGTAAAACGACGGCCAGTGAATTGTAATACGACTCACTATAGGGCGAA TTCGATCGAGGGAAGA GG | (SEQ ID NO:16) |
| Zap-R | AACAGCTATGACCATGATTACGCCAAGCTATTTAGGTGACACTA TAGAATACTCAAGCTTGGATCCGATCGCACGCGGGAG | (SEQ ID NO:17) |

Examples of Gene specific primers (qsp)

| | | |
|---|---|---|
| AT-F | cgagggaagaggTACAGCATCATCTTTGTGGTGGGGA | (SEQ ID NO:18) |
| AT-R | cgcacgcgggagTCGAATTCCGAGACTCATAATGA | (SEQ ID NO:19) |
| Ren-F | cgagggaagaggTAGGTCAGCAACATGGACTATGT | (SEQ ID NO:20) |
| Ren-R | cgcacgcgggagTAGCGGGCCAAGGCGAACC | (SEQ ID NO:21) |
| ACE-F | cgagggaagaggTGCCTCCCCAACAAGACTGCCA | (SEQ ID NO:22) |
| ACE-R | cgcacgcgggagTCCACATGTCTCCCAGCAGATG | (SEQ ID NO:23) |
| GAP-F | cgagggaagaggTCCATGGAGAAGGCTGGGG | (SEQ ID NO:24) |
| GAP-R | cgcacgcgggagTCAAAGTTGTCATGGATGACC | (SEQ ID NO:25) |
| TMB-F | cgagggaagaggTCCNYTNYTNYTNGGNGCNGCNATGGC | (SEQ ID NO:26) |
| TMB-R | cgcacgcgggagTANACCCANGGRTCNARDATYTGRTTCCA | (SEQ ID NO:27) |
| BmTM3-F | cgcccgccgcgcCCCGCGCCC | (SEQ ID NO:28) |
| BmTM7-R | cgcacgcgggagTANARNGCRAANGGRTTNACRCA | (SEQ ID NO:29) |
| XREN-F | cgagggaagaggTTAYGGNGARATHGGNATHGGNACNCC | (SEQ ID NO:30) |
| XREN-R | cgcacgcgggagTYTGNGTNACNGTDATNCCNCCHACNGT | (SEQ ID NO:31) |
| XGA2-F | cgagggaagaggTGCNGGNGARWSNGGNAARWSNAC | (SEQ ID NO:32) |
| XGC2-r | cgcacgcgggagTCNSWNCKYTGNCCNACNACRTC | (SEQ ID NO:33) |
| Go-f | cgagggaagaggATGGGATGTACTCTGAGCGCAGAGG | (SEQ ID NO:34) |
| Go-r | cgcacgcgggagCGCACGCGGGAGTCAAAGTTGTCATGGATGACC | (SEQ ID NO:35) |
| Gq-F | cgagggaagaggATGACTCTGGAGTCCATCATGGCGT | (SEQ ID NO:36) |
| hGs | cgcacgcgggagTCCATGGAGAAGGCTGGGGcc | (SEQ ID NO:37) |
| mG15 | cgagggaagaggATGGCCGGCTGCTGCTGTTTGTCTG | (SEQ ID NO:38) |
| mG11 | cgagggaagaggATGACTCTGGAGTCCATGATGGCGT | (SEQ ID NO:39) |

Vector adapters

| | | |
|---|---|---|
| cZR-RP1 | CTCCCGCGTGC GATCGG TCATAGCTGT TTCCTGTG | (SEQ ID NO:40) |
| ZR-ada | CACAGGAAAC AGCTATGACC GATCGCACGC 6GGAG | (SEQ ID NO:41) |
| cpet ir | CTCCCGCGTG CGATC GGGCTGCTGCCACCGCTGAGC | (SEQ ID NO:42) |
| ZR-adet | GCTCAGCGGT GGCAGCAGCC CGATCGCACG CGGGAG | (SEQ ID NO:43) |
| pET-y | CGGCACCGTC ACCCTGGATGCTGTAGG | (SEQ ID NO:44) |

Vector ampliflying primers

| | | |
|---|---|---|
| M13-FZ | CGA GGG AAG AGG TGGCGATTAAGTTGGGTAACGCC | (SEQ ID NO:45) |
| M13-R | Z GGC ACG CGG GAG TCACACAGGAAACAGCTATGAC | (SEQ ID NO:46) |
| M13-RB (ZF) | CGA GGG AAG AGG TGTGTGGAATTGTGAGCGG | (SEQ ID NO:47) |
| -20 forward | GTAAAACGACGGCCAGT | (SEQ ID NO:48) |
| -47 forward | CGCCAGGGTTTTCCCAGTCACGAC | (SEQ ID NO:49) |
| reverse-48 | GAGCGGATAACAATTTCACACAGG | (SEQ ID NO:50) |
| M13-Q | CGA GGG AAG AGG TGGCGATTAAGTTGGGTAACGCC | (SEQ ID NO:51) |
| M13-RZ | GGC ACG CGG GAG TCACACAGGAAACAGCTATGAC | (SEQ ID NO:52) |
| M13-RB | (ZF) CGA GGG AAG AGG TGTGTGGAATTGTGAGCGG | (SEQ ID NO:53) |
| pZO4 upper | CGAGGGAAGAGGGGCCCcccccccccgggtttaaaaaaaaaaaa | (SEQ ID NO:54) |
| pZO4 lower | CGACGTTTTT TTTTTTTAAA CCCGGGGGGG GGGGGCC | (SEQ ID NO:55) |
| f/r join | CGA GGG AAG AGG T GGC ACG CGG GAG T | (SEQ ID NO:56) |
| GT$_{10\text{-}F}$ | TGT AAA ACG ACG GCC AGT AGC AAG TTC AGC CTG GTT AA | (SEQ ID NO:57) |
| GT$_{10\text{-}R}$ | TCC CAG TCA CGA CGT TGT GGG GTA AAT AAC AGA GGT GGC | (SEQ ID NO:58) |
| GT$_{11}$F | GGT GGC GAC GAC TCC TGG AGC CCG | (SEQ ID NO:59) |
| GT$_{11}$R | TGG ACA CCA GAC CAA CTG GTA ATG | (SEQ ID NO:60) |
| Xt$_3$: | CGA CGG CCA GTC GAC TCT AGT TT | (SEQ ID NO:61) |
| Xt$_4$: | CGA CGG CCA GTC GAC TC | (SEQ ID NO:62) |

TABLE 1-continued

Sequences of oligonucleotides

*Upper case denotes sequences matching PCR template targets. Lower case denotes additional sequence added to facilitate zipper PCR strategies. Sequence is given in IUPAC nomenclature; in some cases, more than one nucleotide is synthesized to permit amplification of multiple gene sequences belonging to a gene family.

Figure 6A:
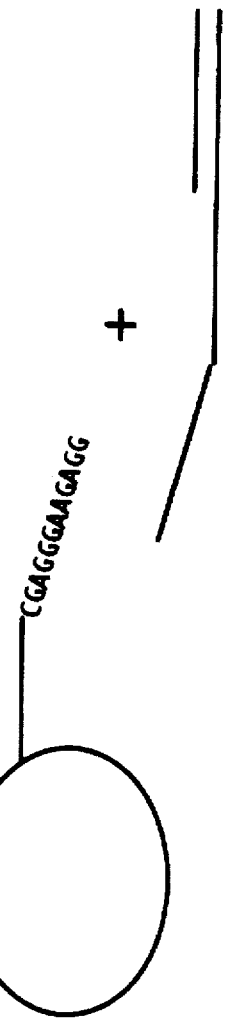
FIG. 6 illustrates joining of zipper-cohesive inserts to solid support. A. Oligonucleotides SEQ ID NO:1), linked through 5' attachments to solid support (such as magnetic beads, polystyrene plastic, sephadex beads, microtiter plates, nylon membrane, glass, etc.), are added to DNA with zipper cohesive ends produced through exonuclease treatment. B. The 3' ends contain zipper sequence and anneal to the cohesive DNA ends containing zipper sequence. C. Extension by polymerase results in double-strand, fully-extended DNA attached to solid support. This DNA can be used in sequencing reactions, as are DNA affinity columns to capture related nucleic acids, or in radioactive and nonradioactive nucleic acid detection. The same procedure illustrated may be used to recombine DNA with numerous other functional groups.
Figure 6B:
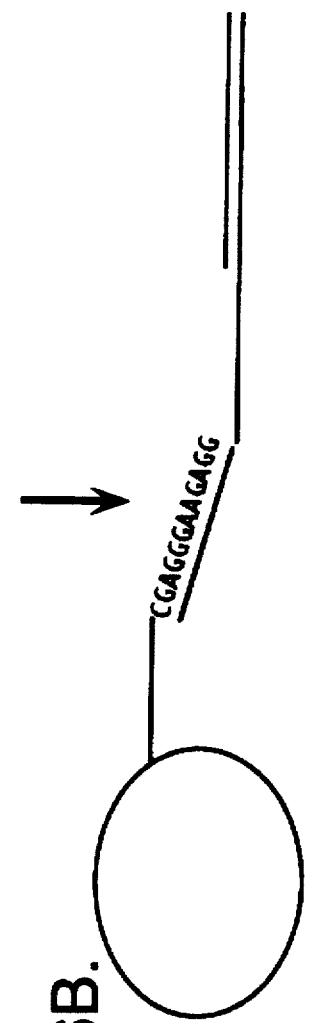
Figure 6C:
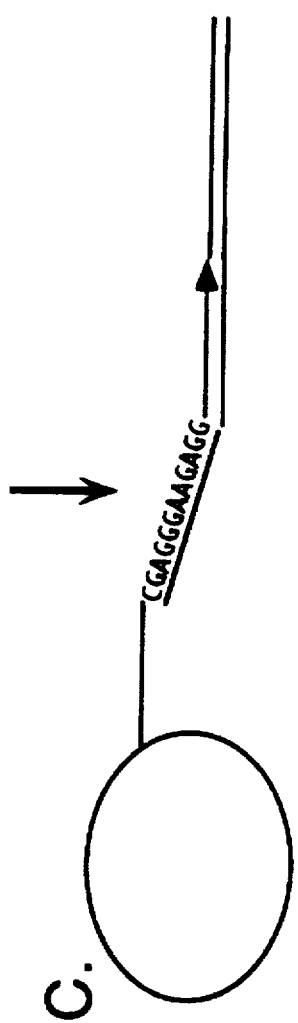

The most flexible adapter sets that have proven most useful in multiple applications are ZAP1-F and ZAP1-R (SEQ ID NOS:16 AND 17) (FIG. 5). ZAP1-F attaches to cohesive ends produced by 5' exonuclease digestion of DNA containing the zipper forward sequence. After extension is complete, an M13 universal sequencing site, a T7 RNA promoter and several restriction sites are incorporated to the DNA. ZAP1-R attaches to the zipper reverse sequence to incorporate an $sp_6$ RNA promoter, an M13 reverse sequencing site, and additional restriction endonuclese sites. ZAP-P* and ZAP-R* represent adapters with the same sequence into which biotin has been incorporated at the 5'. By joining a biotinylated oligonucleotide to one end of DNA and an unbiotinylated oligonucleotide to the other, extended DNA can be bound to streptavidin-coated solid support (FIG. 6). Several different manipulations can then be performed in the solid phase, including cRNA transcription of either strand, and sequencing of DNA. Bead-bound DNA can be gathered, purified, and reused; multiple step molecular manipulations are facilitated since buffers and by-products are quickly exchanged during washing of other bead-bound material. DNA can be reamplified from its solid support or cleaved by restriction endonuclease off the bead. The invention thus extends solid phase sequencing strands of Uhlén and coworkers[22]. Unlike methods in the art, however, only two biotinylated primers are used to bind innumerable different DNAs to solid phase in different experiments. Since as little as 0.5 pmole of adapter has been used to bind sufficient DNA to solid phase for these applications, a 1 pmole synthesis of adapter oligonucleotide is theoretically sufficient for use in $10^6$ experiments. Production of multiple biotinylated primers is a major expense of current solid-phase DNA technology, especially since investigators often remake identical pairs of primers with and without biotin to bind opposite DNA strands to solid support.

In addition to supporting multiple molecular procedures, the sequence of ZAP1-F and ZAP1-R is identical to sequence present at the multiple cloning site of pGEM. Eighteen bases in each ZAP are identical to sequence in M13 and pUC vectors. These sequence identities are the basis of cloning methods discussed in Example 6.

Thus, after extending with ZAP1-F and ZAP1-R adapters, DNA can be easily purified, converted to single-strand probe, transcribed into cRNA, restriction-digested or easily cloned into pGEM-32, M13, pUC plasmid, and related vectors. These applications are all routinely used in our laboratory; over 15 different G protein and G-coupled receptor cDNAs have been manipulated by these methods.

EXAMPLE 5

Joining of Zipper-PCR Products to Adapters Through Secondary PCR

Figure 7:
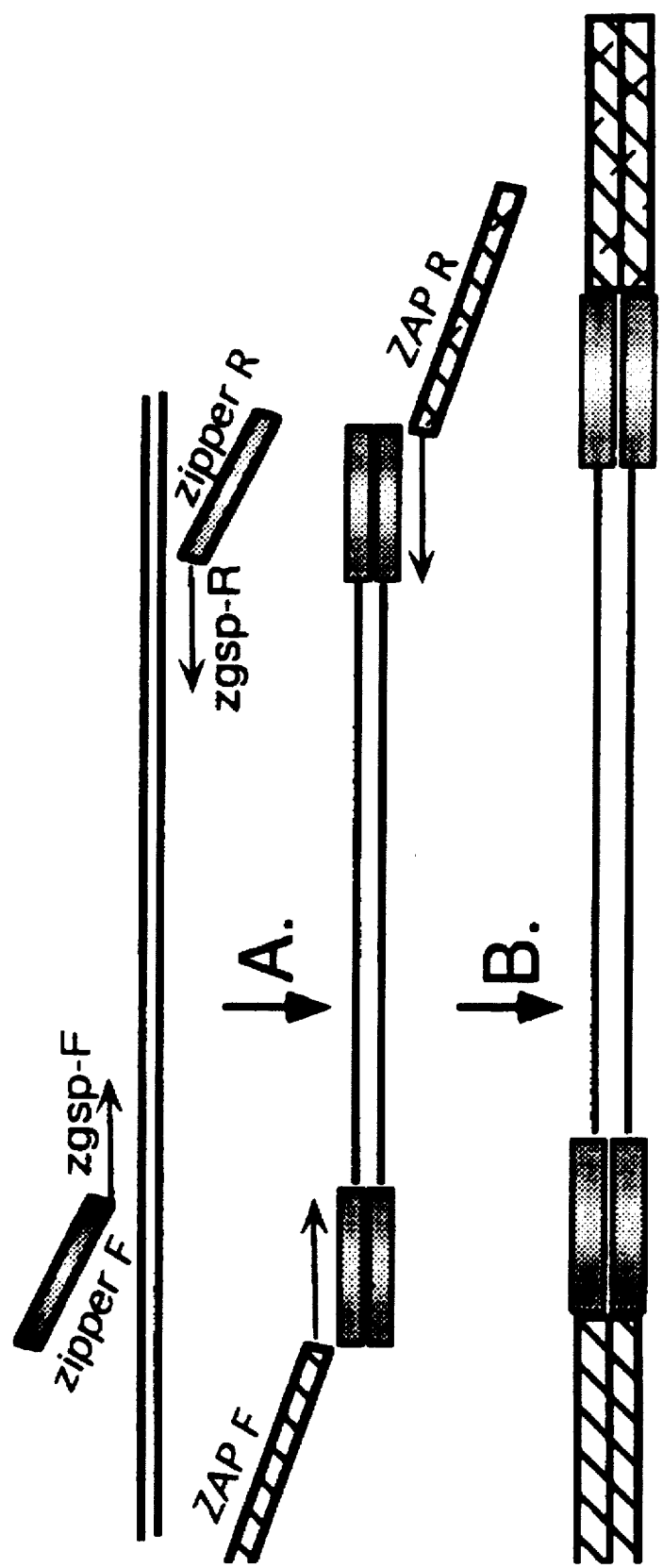
FIG. 7 illustrates introduction of adapters into DNA through secondary PCR. The same zipper sequences and adapters are used as in FIG. 5, except that adapters are used at high concentration to amplify zipper-containing DNA in a secondary (or "piggyback") PCR. A. First PCR primed by zipper-containing gene-specific primer (zgsp) having zipper sequences at 5' (see FIG. 1.A.) yields double-strand DNA. B. Secondary PCR ("piggyback" PCR) primed by ZAP (FIG. 1.B.) targeted to zipper domains introduced during first PCR. The result is double-strand DNA containing the sequences and functional groups introduced through the adapter domain of ZAP.

FIG. 7 depicts the joining of DNA to ZAP primers by a second method, namely through secondary PCR (also referred to as a "piggyback PCR"). Zipper sequences at the extreme ends of PCR products become the target of adapter-primed additional PCR. Several PCR formats have been developed to accomplish this; again, cDNA from many different G proteins have been manipulated using these procedures. In Format 1, an initial round (30 cycles) of PCR are primed by gsp primers under conditions using target-determined amplification parameters. The 5' zipper additions do not appear to impair PCR; indeed, we often observe that the length of ts- primers is more efficient in PCR than similar primers lacking the 12-base zipper additions. A 1-ml aliquot of the product of this amplification is then used as the template in a second round (30 cycles) of PCR primed by the universal primers, using a standard amplification protocol (95° C., 40 s; 53° C., 45 s; 72° C., 60 s).

A second format for adapter attachment is referred to as the 10/25 protocol. This format is designed to keep the number of total PCR cycles low in order to minimize Taq-induced sequence errors during amplification, and to minimize the use of PCR reagents. In this format, an initial round (10 cycles) of PCR is done using a reduced amount of the ts- primers (2 pmol each) in a small volume reaction (total vol—3 ml). Immediately following the initial round, 40 ml of a fresh 1xPCR mixture is added, consisting of standard concentrations of Perkin-Elmer PCR buffer, dNTPs, Mg, fresh Taq DNA polymerase, and 20 pmol each of primers ZAP-F and ZAP-R. PCR is continued for an additional 25–30 cycles, using the same parameters outlined for the second round of format 1.

Although adding adapters by GLUEE and by secondary PCR can result in essentially identical products, each has advantages for different uses. Secondary PCR requires only one enzyme (Taq polymerase) in a format that is familiar to PCR users. However, much more adapter primer is required to drive secondary PCR than is necessary for GLUEE; when larger adapters are required, such as ZAP1-F or ZAP1-R, adapter ligation by GLUEE is much more economical. Since annealing in GLUEE pairs cohesive single strands, a process which proceeds avidly at room temperature, shorter zipper sequences can be used at the 5' of gsp primars (6–12 nucleotides). In contrast, annealing of adapters to denatured double-strand PCR products has been shown to require slightly more extensive overlap; less than 12 nucleotides appear to be inefficient in supporting secondary PCR. In some experiments, GLUEE and secondary PCR can be used sequentially; after ligating adapters onto DNA targets by GLUEE, additional material can be made by secondary amplification primed by additional adapter. When long adapters are required (ZAP1-R is 66 nt and ZAP1-R is 81 nt), oligonucleotide can be conserved by ligating small amounts onto DNA using GLUEE, then reamplifying using secondary PCR primed by a shorter oligonucleotide complementary to sequence at the 5' of the adapter (such as the M13 universal forward and reverse primers incorporated into ZAP1-F and ZXAP1-R.

EXAMPLE 6

Figure 8:
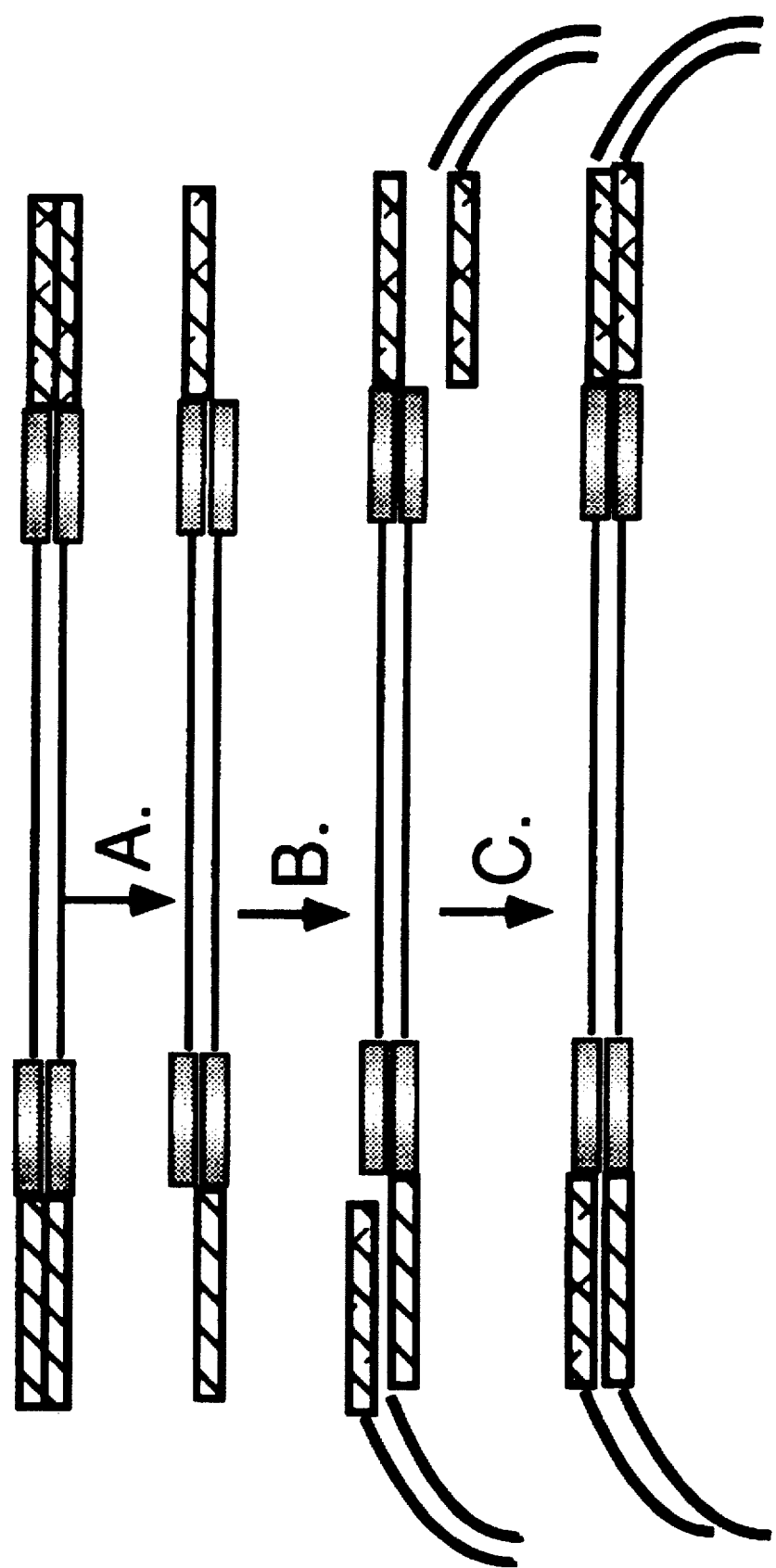
FIG. 8 illustrates cloning of DNA into plasmid vector by the invention. A. Sequence complementary to vector is affixed to zipper-containing DNA by GLUEE (FIG. 4) or secondary PCR (FIG. 7). B. Resulting DNA is briefly treated with exonuclease (5' or 3' digesting) to expose cohesive ends. C. Cohesive DNA is annealed to complementary cohesive ends of vector that has been similarly treated with exonuclease. Annealed DNA is transfected into host cells (bacteria or eukaryotes).

Demonstration of Directional Cloning of cDNA Ligated to ZAPs into Plasmid Vectors in Format A After joining DNA to certain ZAPs (either by GLUEE or by secondary PCR), the DNA can be introduced into vector plasmids or lambda phage. Primer pairs ZAP1-F and ZAP1-R are used to clone DNA into M13, pUV, or pGEN plasmids. Primers RAQ and FAQ introduce DNA into pQE-9, and FAB and RAB are for cloning into pET vectors. In each case, adapters introduce 320–60 bp sequences that match corresponding sequences of vectors (FIG. 8). After brief digestion with either 3' or 5' exonuclease, cohesive ends are generated in the end of vector and insert. Although we have used ExoIII, T7 polymerase (in the absence of dNTPs), and certain lots of T4 DNA polymerase, the preferred enzyme in our laboratory at present is T7 gene 6 exonuclease. DNA (vector linearized by restriction enzyme digestion and insert) was treated for 30 sec to 1.5 min with 1–4 U T7 gene 6 in standard buffers used for amplification. DNA is then heated to 70° C. for 10 min to inactivate enzyme. Vector and insert (10–100 mg each) are then annealed for 10–30 min at room temperature. In some cases, the annealed vector-insert is extended by the addition of fresh polymerase (Klenow fragment, Taq DNA polymerase, etc.) to fill in gapped duplex DNA; this can reduce background from extensively digested vector that inappropriately recircularized. In most cases, however, the gapped vector insert is directly used to transfer bacterial hosts without repair by DNA extension. If gapped DNA is transfected without repair, the vector-insert complex is heated to 70° C. for 10 min prior to transfection to disengage any inappropriately hybridized ends. The extent of vector digestion or the presence of gaps in vector-insert duplex makes little difference in cloning efficiency, as bacterial repair enzymes repair gapped DNA after transformation. We have found on numerous occasions that several hundred clones from 100 mg input DNA can easily be achieved. Background transformation of vector without insert is low or nonexistent, depending primarily on the efficiency of restriction enzyme digestion during the step by which vector was linearized. Background can be further lowered by using two or more restriction enzymes. The system is compatible with blue-white selection in vectors containing lacZ at the cloning site.

The utility of this system has been demonstrated by cloning more than 20 different PCR-amplified DNA into 5 different plasmids (pGEM-3Z, M13 MP18, pUC, pQE-9, and pET-15). Presence of insert has been confirmed by standard plasmid analysis, including restriction digestion and sequence analysis by standard sequenase dideoxysequencing protocols. Orientation of inserts was found to be determined appropriately by the direction of adapter primer joined to DNA. DNA cloned into protein expression vectors (pQE-19 and pET-15) has been appropriately expressed as 6 histidine recombinant fusion protein, and has been purified using methods suggested by the respective vector manufacturers.

It is apparent that the invention could be used to clone DNA into lambda phage vector with equal efficiency or to any other cloning vehicle. Cloning vehicles do not need to be altered; insert DNA need only be joined to adapter-containing vector complementary sequence. It is also apparent that aliquots of one reaction of PCR-generated DNA can be joined to several different vector-specific adapters and cloned simultaneously to several different cloning vehicles with specialized uses. We have constructed four different cDNA libraries from mRNA derived from small cell lung tumors after reverse transcription (RT) PCR amplification using mixed oligonucleotide primers. It is also evident that directional cloning by the invention can be used to construct cDNA libraries without PCR.

EXAMPLE 7

Demonstration of Directional of cDNA into Modified Vectors Cloning in Format B

Example 6 demonstrates cloning of ZAP-joined DNA into unmodified vectors. In a variation of this procedure, we have simply introduced the 12-base zipper sequence into the plasmid vector so that primary PCR products may be cloned without the use of ZAPs. Zipper sequences have been introduced into vectors (including pQE-9, pGEM-32, pET-15, and M13 MP18) using both standard and novel techniques. Resulting modified zipper-containing vectors have been named pZQE-9, pZGEM, pZET, and pZM13, respectively. Methods of vector modification are outlined below.

A. Creation of pZGEM by Genetic Engineering (FIG. 9).

Sequences to be introduced into vector were made on an ABI 394 oligonucleotide synthesizer (Applied Biosystems, Foster City, Calif.). Two overlapping oligonucleotides were made, with complementary sequence containing zipper sequences, Apa 1 restriction site, and EcoR1 and HindIII compatible cohesive ends (SEQ ID NOS:63 and 64). Oligonucleotides were desalted and used without gel purification. 5' Terminal phosphates were added to oligonucleotides with T4 polynucleotide kinase and ATP under standard conditions[13]. After kinase treatment, oligonucleotides were heated to 70° C. for 10 min; 50 ng of each oligonucleotide were annealed together at 65° C. for 20 min and cooled to room temperature. The vector pQE-9 was digested with BamHI and HindIII, and the linearized vector gel-purified. Vector and annealed oligonucleotides were combined in a 10-ml reaction mix with freshly diluted ATP and DNA ligase (BRL, Bethesda, Md.) using conditions specified by the manufacturer. After ligation overnight at 16° C., the DNA was transformed into competent E. coli HB1-01 cells (BRL), and transformed cells were plated on LA-ampicillin plates. Seventy-five colonies were found to result. Standard preparation of plasmid DNA from 3 of these colonies using DNA purification columns (Qiagen, Foster City, Calif.) followed by standard sequencing protocols (Sequinase, U.S. Biochemical, Cleveland, Ohio) demonstrated the expected sequence.

B. Introduction of Zipper Sequence into pGEM03Z via Exonuclease Cloning.

A simpler procedure was used to introduce zipper sequence into plasmid: pQE-9 simultaneously with the protein expression cloning of the mouse G protein $b_3$ subunit. In this procedure, Apa 1 restriction sites were added at the junction of zipper and gsp sequences in the amplifying primer. After amplification of the 1076 bp $b_3$ open reading frame (ORF) from a mouse plasmid clone in pGEM-32 (generously provided by Dr. Mike Levine, Johns Hopkins University, Baltimore, Md.), the cDNA was cloned into Bam-HindIII digested pQE-9 linear vector using methods outlined above. After the resulting plasmid was selected, grown, and purified, the insert was released by digesting at the introduced Apa 1 site flanking both ends of insert (FIG. 10). After gel purification, the linearized vector was demonstrated to have zipper sequence present at each end.

C. Cloning of DNA into Zipper-Containing Vector.

Zipper sequences introduced into vectors by conventional or exonuclease cloning methods are available for cloning. Procedures are similar to Example 6. DNA bearing the forward zipper sequence (6–12 nt) on one end and the reverse zipper sequences (6–12 nt) on the other are digested briefly (0.5–1.5 min) with exonuclease (T7 gene 6 product is preferred). Vector-containing zipper sequences are digested in an identical manner. Ten-100 mg of vector and DNA insert so treated are annealed 20 min-2 hr in 10 ml standard amplification buffer and used to transform competent E. coli by standard methods.

The cloning methods of Examples 6 and 7 have different advantages for particular experiments. In most cases, unmodified wild type vector is the preferred cloning vehicle when initiating a series of experiments and, as the addition of vector-containing ZAPs to insert DNA permits cloning into any unmodified vector to which sequence is known, the method of Example 6 is chosen. However, if an investigator wishes to repetitively use a particular vector in a long series of experiments, cloning into zipper-modified vector will be preferred (Example 7), as adapters need not be added to the PCR-generated DNA by either GLUEE or secondary PCR.

It should be noted that the GLUEE procedure can be used to modify vector DNA as well as PCR-generated DNA. This will provide another simple means to add zipper sequence to wild-type vector. It also demonstrates a means of adding special modified nucleotides and functional sequences to vectors without cloning

EXAMPLE 8

Release of Zipper cDNA from Vector and Shuttle-Cloning into other Zipper-Vector Constructs DNA inserts in zipper-vectors have been constructed so that they can be released from plasmid with the zipper intact so that, after treatment with exonuclease, cohesive zipper sequence ends are regenerated and DNA can be joined to other ZAPs and cloned into other zipper vectors. A Pvu 1 site has been engineered at each junction of vector and zipper sequence (FIG. 11). This is not to be confused with the Apa 1 site at the zipper-insert junction. Thus, the order of sequences is vector, Pvu 1, zipper forward, Apa 1, insert, Apa 1, zipper reverse, Pvu 1, vector. Digestion of vector in which zipper inserts reside by Apa 1 leaves the zippers joined to vector (Example 7). Digestion with Pvu 1 releases insert with zippers intact (current example).

The purpose of regenerating zipper-cohesive DNA adds great flexibility to this system. Although DNA inserts could easily be reamplified for further recombinant experiments calling for modifications in sequence or chemical modifications of DNA ends, it is known that unwanted mutations can be introduced into DNA during amplification by Taq DNA polymerase. This may be especially relevant when isolating clones from cDNA libraries in zipper-modified lambda phage. In such cases, it will usually be necessary to subclone inserts into plasmids. Reamplification before subcloning may introduce errors that could distort DNA analysis. The ability to regenerate zipper-cohesive ends facilitates rapid shuttle subcloning without the risk of Taq-induced errors.

EXAMPLE 9

Introduction of Uridine-Containing Adapters into Zipper-DNA for Rapid Cloning

One special application of procedures illustrated in Examples 3 and 4 is the use of GLUEE and secondary PCR to introduce ZAP-containing uridine. This procedure has been used to subclone portions of the human and baboon thrombin receptors, and G proteins $G_{11}$ and $G_{14}$ in this laboratory. The UDG cloning method exists in the art and has been shown to be highly effective. However, that method requires that many PCR primers be synthesized with uridine residues, which is inefficient and expensive. In the current invention, we have synthesized ZAP primers (U-FOR and U-REV) that bind to cohesive zipper ends. After incorporation to DNA, the resulting construct can be digested with UNG according to the directions of the manufacturer (BRL). In one example, >700 colonies were obtained from 75 ng of 700 bp segment of human $G_{11}$ cDNA cloned by this method.

This example demonstrates that the ZAP methods can augment many protocols existing in the art. The key advantage of the invention is the reduction in number and types of primers that needs to be synthesized. Regardless of whether uridines, biotins, etc., need to be incorporated into a given DNA, such groups can be attached with a minimum of effort using the catalogued adapters.

EXAMPLE 10

Introduction of Zipper Sequences into Non-Amplified DNA

Figure 13A:
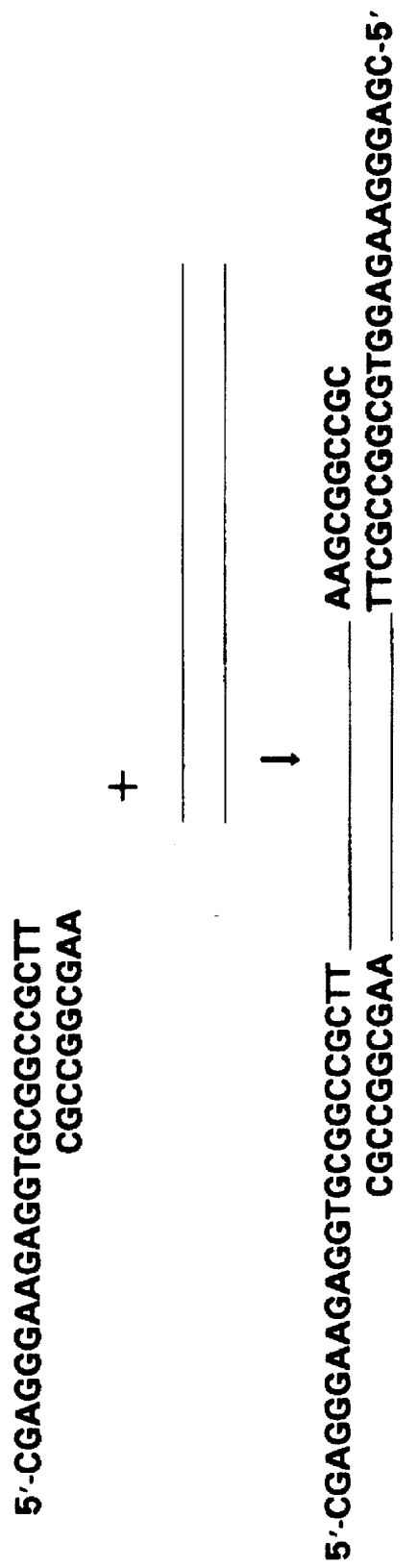
FIG. 13 illustrates introduction of zipper sequences into DNA that have not been amplified. Although the current invention is primarily intended as a method to manipulate and clone DNA produced by amplification, zippers and adapters can be introduced into other nonamplified DNAs using ligase. Zipper sequences can also be introduced at the 5' of oligonucleotides used to prime mRNA via reverse transcriptase into cDNA. Second-strand cDNAs can be joined to a second zipper by tailing or ligation. The examples of FIG. 13 are described by SEQ ID NOS: 65–74.

Although many aspects of the current invention have been designed for practical use with PCR-generated DNA, it is evident that the invention will work well with any DNA to which the common-denominator 6–12 base zipper sequences have been added. Many methods exist in the art for such additions; genome DNA can be digested with restriction endonucleases to generate 2–6 base cohesive ends. Oligonucleotide adapters have been constructed so that the 6–12 base zipper sequences can be added to such DNA by standard ligation (FIG. 13) (SEQ ID NOS:65–74). Blunt end adapters can also be used to adjoin sequences to blunt-end-digested genomic or cloned DNA.

Zipper sequences can also be added to cDNA during reverse transcription (RT) of mRNA using standard techniques, such that 6–12 bases can be added to the 5' of poly-dT oligonucleotide used to prime mRNA RT. Additional sequence can be added to the 5' of cDNA by tailing reactions or by ligation with RNA or DNA ligase.

Regardless, once defined zipper sequences have been added to nucleic acids, resulting molecules can be modified by ZAPs and cloned to zipper vectors. Guanine DNA cut by one restriction enzyme or produced by sonication will not be directionally manipulated by these procedures, as ligation will result in symmetrical placement of an adapter at both ends. However, genomic DNA cut by two zippers, and cDNA reverse transcombined by zipper-oligo dT can be directionally cloned and manipulated. Again, it is evident that zipper methods detailed in this invention will serve as useful adjuncts to many protocols currently in the art. It is evident that cloning of both genomic DNA and cDNA will be greatly enhanced by extending cohesive ends for the currently available 2–4 bases generated by restriction enzymes to 6–12 bases by zipper methods.

EXAMPLE 11

Enhanced Long-Distance Sequencing of PCR Products

Example 1 (FIG. 2) presents a simple method for selectively converting amplified DNA to single strands. It is evident that this invention can be used for extending and enhancing dideoxysequencing of PCR-amplified DNA. If at least 5 uridines are uncompartmented at the 5' of 1 primer but not the other in a pair of gene-specific primers used to amplify DNA, or joined to the DNA by GLUEE or secondary PCR, a highly stable 3' overhang can be created in the resulting PCR product by treatment with UNG enzyme (FIG. 14). This 3' overhang can protect that end of DNA from the 3' exonuclease activity of ExoIII enzyme. Addition of exonuclease III (ExoIII) to the PCR product selectively degrades the 3' of the other end. Fixed digestion of PCR product will result in progressive shortening of this end. After halting such reaction, the PCR strand can be reextended in the presence of fluorescent or radioactively-labeled nucleotides mixed with dideoxynucleotides, resulting in accumulation of DNA sequence information when said reactions are electrophoresed on acrylamide gel according to standard procedures.

Methods using the activity of ExoIII exist in the art for creating sets of nested clones that are useful in sequencing (as popularized by Strategene Corp., La Jolla, Calif.). In these procedures, protective 3' overhangs are created by restriction endonuclease digestion at one end of plasmid DNA, and ExoIII-susceptible 5' overhangs are created at the opposite DNA ends. These methods usually require that the progressively shortened DNA be subsequently "polished" with mung bean nuclease or similar endonuclease, circularized and cloned. Other investigators have directly sequenced ExoIII-treated plasmids and cosmids after double restriction digestion and treatment with additional enzymes, including methalases. However, such procedures have not been easily applied to sequencing of PCR products, especially because 3' overhang-producing restriction enzymes do not easily cut the ends of PCR products. Thus, the merit of this example is that we have demonstrated that a highly reliable 3' overhang can be produced that selectively protects DNA ends against ExoIII digestion. After such a protective end is generated, we have found methods in the art highly useful for selectively sequencing long distances of amplified DNA.

From the foregoing, it can be seen that, although specific embodiments of the invention have been described as a means of illustration, many different variations can be made and proposed without deviating from the spirit and scope of the invention.

REFERENCES

1. Saiki, R K, Walsh D S, Erlich, H A. *Proc. Natl. Acad. Sci. USA* 1989;86:6230-4
2. White T J, Madej, R, Persing D H. *Adv. Clin. Chem.* 1992;29:161-96
3. Persing D H. *J. Clin. Microbial.* 1991;29:1281-5
4. Maniatis et al. *Molecular Cloning: A Laboratory Manual.* Cold Spring Harbor, N.Y.: Cold Spring Harbor Laboratory, 1983
5. Jung V, Pestka S B, Pestka S. *Nucleic Acid Res* 18:6156
6. Saiki R K, Walsh D S, Erlich H A. *Proc Natl Acad Sci USA* 1989;86;:6230-4
7. Zhang Y, Coyne M Y, Will S G, Levenson C H, Kawasaki E S. *Nucleic Acids Res.* 1991;19:3929-33
8. Helmuth R. Nonisotopic detection of PCR products. In: Innis M A, Gelland D H, Sninsky J J, White T J (eds.), *PCR Protocols: A Guide to Methods and Applications.* San Diego, Calif.: Academic Press, pp. 119-28, 1990.
9. Gyllensten U B, Erlich H A. *Proc Natl Acad Sci USA* 1988;85:7652-56
10. Stoker A W. *Nucleic Acid Res* 1990;13:4290
11. Aslanidis C, de Jong P. *Nucleic Acids Res* 1990;18:6069-74
12. Kuijper *Gene* 1992;112:147-55
13. Haun R S et al. *BioTechniques* 1992;13:515-8
14. Haun R, Moss J. *Gene.* 1992;112:37-43
15. Pham T, Cheng Q L. CLONTECHques 1993;8:5-9
16. Kaluz S, Kolble K, Reid K B. *Nucleic Acids Res* 1992:204369-70
17. Lindahl T, Ljungquist S, Siegert W, Nyberg B, Sperens B. *J Biol Chem* 1977;252:3286-94
18. Rashtchian A, Buchman G W, Schuster D M, Berninger M S. *Anal Biochem* 1992;206:91-7
19. Rashtchian A, Thornton C G, Heidecker G. *PCR Methods Appl* 1992;2:124-30
20. Nisson P E, Rashtchian A, Watkins P C. *PCR Methods Appl* 1991;1:120-3
21. Mitchell and Herrill *Anal Biochem* 1989;178:239-42
22. Uhlén *Proc Natl Acad Sci USA* 1990;87:6569-73
23. Kerr, C, Sadowski P D. *J Biol Chem* 1972;47:311-8
24. Straus, N. A., & Zagursky, R. J. *Biotechniques* 1991;10:376-84
25. Anderson L J, Gary W G, Young N. Human parvovirus B19. In Lennette ED (ed.) *Laboratory Diagnosis of Viral Infections.* Marcel Dekker, New York, pp. 627-42, 1992
26. Török T J. Parvovirus B 19 and human disease. *Adv Intern Med* 1992;37:431-455
27. Durigon E L, Erdman D D, Gary G W, Pallansch M P, Torok T J, Anderson J J. *J. Virol, Methods* (in press).
28. Török T J, Wang Q Y, Gary G W, Yang C F, Finch T M, Anderson L J. *Clin Infect Dis* 1992;14:49-53
29. de Noronha C M, Mullins J I. *PCR Methods Appl* 1992;2:131-6
30. Eisenach K D, Sifford N D, Cave N D, Bates J H, Crawford J T. *Ann Rev Respir Dis* 1991; 144:1160-3
31. Böddinghaus B, Rogall T, Flohr T, Blöcker H, Böttger E C. *J Clin Microbiol* 1990;28:1942-6
32. Woese C R. *Microbial Rev* 1987;51:221-71
33. Wilson K H, Blitchtngton R B, Greene R C. *J Clin Microbiol* 1990;28:1942-6
34. Roberts G D, Goodman N L, Helfets L, Larsh H W, Lindner T H, McClatchy J K, McGinnis M R, Siddiqi S H, Wright P. *J Clin Microbiol* 1983;18:689-96
35. Drake T, Hindler J A, Barton G W, Bruckner D A. *J Clin Microbiol* 1987;25:1442-5
36. Evans K D, Nakasome A S, Sutherland P A, DeLaMaza L M, Peterson E M. *J Clin Microbiol* 1992;30:2472-31
37. Jarolim P et al. *Proc Natl Acad Sci USA* 1991;88:11022-6
38. Guo L H, Wu R. *Nucleic Acids Res* 1982;10:2065-84
39. Guo L H, Wu R. *Methods Enzymol* 1983;100:60-9
40. Henikoff S. *Gene* 1984;28:351-9
41. Sorge J A, Biinderman L A. *Proc Natl Acad Sci USA* 1989;86:9208-12
42. Li C, Tucker P W. *Nucleic Acids Res* 1993;21.1239-44

What is claimed is:

1. A method of adapting a nucleic acid for sequencing comprising:
   a. amplifying the nucleic acid using a first primer containing deoxyuridine monophosphate and a second primer not containing deoxyuridine monophosphate to yield a double-stranded DNA with a polyuridylated 5' end on one strand;
   b. Partially disassociating the resultant double-stranded DNA with uracil DNA glycosylase to form a 3' overhang on the polyuridylated 5' end;
   c. digesting the double-stranded DNA with a 3' exonuclease which digests only the 3' strand from the end opposite the polyuridylated 5' end for a time sufficient to convert at least a portion of the double-stranded DNA to a single-stranded DNA; and
   d. extending the partially digested 3' strand with a polymerase such that sequencing by a dideoxynucleotide process can be performed on the single-stranded DNA.

2. The method of claim 1, wherein the 3' exonuclease is exonuclease III.

3. The method of claim 1, wherein digestion continues for a time sufficient to convert the entire double-stranded DNA to single-stranded DNA, and further comprising the step of binding the single-stranded DNA with a nucleic acid primer which selectively hybridizes with the single-stranded DNA, such that sequencing by a dideoxynucleotide process can be performed on the single-stranded DNA.

4. A method of adapting a nucleic acid for detecting a nucleotide sequence within a double-stranded DNA in a sample, detecting a nucleotide sequence in a sample, inserting a double-stranded DNA into a vector, inserting a target DNA into a target vector, or recombination with a vector comprising:
   a. amplifying the nucleic acid using a first primer containing deoxyuridine monophosphate and a second primer not containing deoxyuridine monophosphate to yield a double-stranded DNA with a polyuridylated 5' end on one strand;
   b. partially disassociating the resultant double-stranded DNA with uracil DNA glycosylase to form a 3' overhang on the polyuridylated 5' end; and
   c. digesting the double-stranded DNA with a 3' exonuclease which digests only the 3' strand from the end opposite the polyuridylated 5' end for a time sufficient to convert at least a portion of the double-stranded DNA to a single-stranded DNA.

5. The method of claim 4, wherein the 3' exonuclease is exonuclease III.

6. The method of claim 4 wherein the nucleic acid is adapted for detecting a nucleotide sequence within a double-stranded DNA in a sample.

7. The method of claim 4 wherein the nucleic acid is adapted for detecting a nucleotide sequence in a sample.

8. The method of claim 1 wherein the nucleic acid is adapted for inserting a double-stranded DNA into a vector.

9. The method of claim 4 wherein the nucleic acid is adapted for inserting a target DNA into a target vector.

10. The method of claim 4 wherein the nucleic acid is adapted for recombination with a vector.

* * * * *

SEQUENCE LISTING ( 1 ) GENERAL INFORMATION:

( i i i ) NUMBER OF SEQUENCES: 75

( 2 ) INFORMATION FOR SEQ ID NO:1:

( i ) SEQUENCE CHARACTERISTICS:
        ( A ) LENGTH: 12 base pairs
        ( B ) TYPE: nucleic acid ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:1:

CGAGGGAAGA GG                                                                          12

( 2 ) INFORMATION FOR SEQ ID NO:2:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:2:

CGCACGCGGG AG                                                                          12

( 2 ) INFORMATION FOR SEQ ID NO:3:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:3:

AGTAATTCCG GACAACGCTC                                                                  20

( 2 ) INFORMATION FOR SEQ ID NO:4:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:4:

TTTCACGAAC AACGCGACAA                                                                  20

( 2 ) INFORMATION FOR SEQ ID NO:5:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:5:

ACGGTGCCCG CAAAGTGTGG                                                                  20

( 2 ) INFORMATION FOR SEQ ID NO:6:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:6:

ACCGTGAGGG CATCGAGGTG                                                                           20

( 2 ) INFORMATION FOR SEQ ID NO:7:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGCCCGCCGC GCCCCGCGCC CGGCCCGCCG CCCCCGCCGG GCCCGAGGGA AGAGG           55

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AGGGAGACCG GAATTCGGAT CCCATATGGC GGCCGCGATC GAGGGAAGAG G                51

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GACAGAGCAC AGAATTCGGA TCCAAGCTTC GATCGCACGC GGGAG                       45

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CAUCAUCAUC AUCAUCAUGC GATCGAGGGA AGAGG                                  35

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CUACUACUAC UACGATCGCA CGCGGGAG                                          28

( 2 ) INFORMATION FOR SEQ ID NO:12:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

CATCATCACA GCAGCGGCCT GGTGCCGCGC GGCGGCGCGA TCGAGGGAAG AGG           53

( 2 ) INFORMATION FOR SEQ ID NO:13:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

TCAGCTTCCT TTCGGGCTTT GTTAGCAGCC GGATCCGATC GCACGCGGGA G             51

( 2 ) INFORMATION FOR SEQ ID NO:14:

( i ) SEQUENCE CHARACTERISTICS:
      ( A ) LENGTH: 57 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:14:

AACTATGAGA GGATCGCATC ACCATCACCA TCACGGATCC TCGATCGAGG GAAGAGG       57

( 2 ) INFORMATION FOR SEQ ID NO:15:

( i ) SEQUENCE CHARACTERISTICS:
      ( A ) LENGTH: 56 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:15:

GGATCTATCA ACAGGAGTCC AAGCTCAGCT AATTAAGCTT CGATCGCACG CGGGAG        56

( 2 ) INFORMATION FOR SEQ ID NO:16:

( i ) SEQUENCE CHARACTERISTICS:
      ( A ) LENGTH: 66 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:16:

TGTAAAACGA CGGCCAGTGA ATTGTAATAC GACTCACTAT AGGGCGAATT CGATCGAGGG    60

AAGAGG                                                               66

( 2 ) INFORMATION FOR SEQ ID NO:17:

( i ) SEQUENCE CHARACTERISTICS:

(A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
AACAGCTATG ACCATGATTA CGCCAAGCTA TTTAGGTGAC ACTATAGAAT ACTCAAGCTT    60

GGATCCGATC GCACGCGGGA G                                              81
```

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CGAGGGAAGA GGTACAGCAT CATCTTTGTG GTGGGGA                             37
```

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
CGCACGCGGG AGTCGAATTC CGAGACTCAT AATGA                               35
```

(2) INFORMATION FOR SEQ ID NO:20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CGAGGGAAGA GGTAGGTCAG CAACATGGAC TATGT                               35
```

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CGCACGCGGG AGTAGCGGGC CAAGGCGAAC C                                   31
```

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:22:

CGAGGGAAGA GGTGCCTCCC CAACAAGACT GCCA 34

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CGCACGCGGG AGTCCACATG TCTCCCAGCA GATG 34

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CGAGGGAAGA GGTCCATGGA GAAGGCTGGG G 31

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CGCACGCGGG AGTCAAAGTT GTCATGGATG ACC 33

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CGAGGGAAGA GGTCCN Y TN Y TN Y TNG- 39
GNGC NGCNATGGC (2) INFORMATION FOR SEQ ID NO:27:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:27:

CGCACGCGGG AGTANACCCA NGGRTCNARD AT Y TGRTTCC A                                  41

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

CGCCCGCCGC GCCCCGCGCC C                                                          21

( 2 ) INFORMATION FOR SEQ ID NO:29:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

CGCACGCGGG AGTANARNGC RAANGGRTTN ACRCA                                           35

( 2 ) INFORMATION FOR SEQ ID NO:30:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CGAGGGAAGA GGTTA Y GGNG ARATHGGNAT HGGNACNCC                                     39

( 2 ) INFORMATION FOR SEQ ID NO:31:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CGCACGCGGG AGT Y TGNGTN ACNGTDATNC CNCCNACNGT                                    40

( 2 ) INFORMATION FOR SEQ ID NO:32:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CGAGGGAAGA GGTGCNGGNG ARWSNGGNAA RWSNAC                                          36

( 2 ) INFORMATION FOR SEQ ID NO:33:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CGCACGCGGG AGTCNSWNCK YTGNCCNACN ACRTC        35

( 2 ) INFORMATION FOR SEQ ID NO:34:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

CGAGGGAAGA GGATGGGATG TACTCTGAGC GCAGAGG        37

( 2 ) INFORMATION FOR SEQ ID NO:35:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CGCACGCGGG AGCGCACGCG GGAGTCAAAG TTGTCATGGA TGACC        45

( 2 ) INFORMATION FOR SEQ ID NO:36:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

CGAGGGAAGA GGATGACTCT GGAGTCCATC ATGGCGT        37

( 2 ) INFORMATION FOR SEQ ID NO:37:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

CGCACGCGGG AGTCCATGGA GAAGGCTGGG GCC        33

( 2 ) INFORMATION FOR SEQ ID NO:38:

( i ) SEQUENCE CHARACTERISTICS:
        ( A ) LENGTH: 37 base pairs
        ( B ) TYPE: nucleic acid (C) STRANDEDNESS: single
          (D) TOPOLOGY: linear (ii) MOLECULE TYPE: DNA (genomic)

(xi) SEQUENCE DESCRIPTION: SEQ ID NO:38:

CGAGGGAAGA GGATGGCCGG CTGCTGCTGT TTGTCTG                    37

(2) INFORMATION FOR SEQ ID NO:39:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:39:

CGAGGGAAGA GGATGACTCT GGAGTCCATG ATGGCGT                    37

(2) INFORMATION FOR SEQ ID NO:40:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:40:

CTCCCGCGTG CGATCGGTCA TAGCTGTTTC CTGTG                      35

(2) INFORMATION FOR SEQ ID NO:41:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:41:

CACAGGAAAC AGCTATGACC GATCGCACGC GGGAG                      35

(2) INFORMATION FOR SEQ ID NO:42:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:42:

CTCCCGCGTG CGATCGGGCT GCTGCCACCG CTGAGC                     36

(2) INFORMATION FOR SEQ ID NO:43:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (genomic)

( x i ) SEQUENCE DESCRIPTION: SEQ ID NO:43:

GCTCAGCGGT GGCAGCAGCC CGATCGCACG CGGGAG   36

( 2 ) INFORMATION FOR SEQ ID NO:44:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

CGGCACCGTC ACCCTGGATG CTGTAGG   27

( 2 ) INFORMATION FOR SEQ ID NO:45:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

CGAGGGAAGA GGTGGCGATT AAGTTGGGTA ACGCC   35

( 2 ) INFORMATION FOR SEQ ID NO:46:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

GGCACGCGGG AGTCACACAG GAAACAGCTA TGAC   34

( 2 ) INFORMATION FOR SEQ ID NO:47:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CGAGGGAAGA GGTGTGTGGA ATTGTGAGCG G   31

( 2 ) INFORMATION FOR SEQ ID NO:48:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

GTAAAACGAC GGCCAGT   17

( 2 ) INFORMATION FOR SEQ ID NO:49:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) SEQUENCE DESCRIPTION: SEQ ID NO:49:

CGCCAGGGTT TTCCCAGTCA CGAC                                                                 2 4

( 2 ) INFORMATION FOR SEQ ID NO:50:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:50:

GAGCGGATAA CAATTTCACA CAGG                                                                 2 4

( 2 ) INFORMATION FOR SEQ ID NO:51:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:51:

CGAGGGAAGA GGTGGCGATT AAGTTGGGTA ACGCC                                                     3 5

( 2 ) INFORMATION FOR SEQ ID NO:52:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:52:

GGCACGCGGG AGTCACACAG GAAACAGCTA TGAC                                                      3 4

( 2 ) INFORMATION FOR SEQ ID NO:53:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:53:

CGAGGGAAGA GGTGTGTGGA ATTGTGAGCG G                                                         3 1

( 2 ) INFORMATION FOR SEQ ID NO:54:

( i ) SEQUENCE CHARACTERISTICS:
      ( A ) LENGTH: 44 base pairs
      ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

CGAGGGAAGA GGGGCCCCCC CCCCCGGGT TTAAAAAAAA AAAA    44

( 2 ) INFORMATION FOR SEQ ID NO:55:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

CGACGTTTTT TTTTTTAAA CCCGGGGGGG GGGGGCC    37

( 2 ) INFORMATION FOR SEQ ID NO:56:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

CGAGGGAAGA GGTGGCACGC GGGAGT    26

( 2 ) INFORMATION FOR SEQ ID NO:57:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

TGTAAAACGA CGGCCAGTAG CAAGTTCAGC CTGGTTAA    38

( 2 ) INFORMATION FOR SEQ ID NO:58:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

TCCCAGTCAC GACGTTGTGG GGTAAATAAC AGAGGTGGC    39

( 2 ) INFORMATION FOR SEQ ID NO:59:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

GGTGGCGACG ACTCCTGGAG CCCG  24

( 2 ) INFORMATION FOR SEQ ID NO:60:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

TTGACACCAG ACCAACTGGT AATG  24

( 2 ) INFORMATION FOR SEQ ID NO:61:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

CGACGGCCAG TCGACTCTAG TTTTTTTTTT TT  32

( 2 ) INFORMATION FOR SEQ ID NO:62:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

CGACGGCCAG TCGACTC  17

( 2 ) INFORMATION FOR SEQ ID NO:63:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

GATCCATCGA GGGAAGAGGG CCCTCTCCC GCGTGCCA  38

( 2 ) INFORMATION FOR SEQ ID NO:64:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

GTAGCTCCCT TCTCCCGGG AGAGGGCGCA CGGTTCGA  38

(2) INFORMATION FOR SEQ ID NO:65:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

CGAGGGAAGA GGTGCGGCCG CTT        23

(2) INFORMATION FOR SEQ ID NO:66:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

CGCCGGCGAA        10

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

CGAGGGAAGA GGTGCGGCCG C        21

(2) INFORMATION FOR SEQ ID NO:68:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

CGCCGGCGTT AA        12

(2) INFORMATION FOR SEQ ID NO:69:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

CGCCGGCGCT AG        12

(2) INFORMATION FOR SEQ ID NO:70:

(i) SEQUENCE CHARACTERISTICS:
        (A) LENGTH: 12 base pairs
        (B) TYPE: nucleic acid ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:70:

CGCCGGCGTC GA                                                                                    12

( 2 ) INFORMATION FOR SEQ ID NO:71:

( i ) SEQUENCE CHARACTERISTICS:
            ( A ) LENGTH: 8 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:71:

GCGGCCGC                                                                                         8

( 2 ) INFORMATION FOR SEQ ID NO:72:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:72:

AATTGCGGCC GC                                                                                    12

( 2 ) INFORMATION FOR SEQ ID NO:73:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:73:

GATCGCGGCC GC                                                                                    12

( 2 ) INFORMATION FOR SEQ ID NO:74:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:74:

AGCTGCGGCC GC                                                                                    12

( 2 ) INFORMATION FOR SEQ ID NO:75:

( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:75:

AAGCGGCCGC                                                                                         10